(12) United States Patent
Dolphin et al.

(10) Patent No.: US 11,517,677 B2
(45) Date of Patent: Dec. 6, 2022

(54) EPIDURAL DEVICE FOR DETECTION OF AND NEEDLE PLACEMENT IN EPIDURAL SPACE

(71) Applicant: Guidestar Medical Devices, Victoria (CA)

(72) Inventors: Michael D. Dolphin, Victoria (CA); Brianna B. Carrels, Victoria (CA); Simon F. Cooke, Victoria (CA); James A. Helliwell, Victoria (CA)

(73) Assignee: GUIDESTAR MEDICAL DEVICES, Victoria (CA)

( * ) Notice: Subject to any disclaimer, the term of this patent is extended or adjusted under 35 U.S.C. 154(b) by 0 days.

(21) Appl. No.: 17/637,791

(22) PCT Filed: Aug. 21, 2020

(86) PCT No.: PCT/CA2020/051147
§ 371 (c)(1),
(2) Date: Feb. 23, 2022

(87) PCT Pub. No.: WO2021/035341
PCT Pub. Date: Mar. 4, 2021

(65) Prior Publication Data
US 2022/0265936 A1 Aug. 25, 2022

Related U.S. Application Data

(60) Provisional application No. 63/039,951, filed on Jun. 16, 2020, provisional application No. 62/891,313, filed on Aug. 24, 2019.

(51) Int. Cl.
*A61M 5/46* (2006.01)
*A61M 5/315* (2006.01)
(Continued)

(52) U.S. Cl.
CPC ...... *A61M 5/31501* (2013.01); *A61M 5/1454* (2013.01); *A61M 5/14526* (2013.01);
(Continued)

(58) Field of Classification Search
CPC .......... A61M 5/31501; A61M 5/14526; A61M 5/1454; A61M 5/46; A61M 5/3146;
(Continued)

(56) References Cited

U.S. PATENT DOCUMENTS

| 5,480,389 A | 1/1996 | McWha et al. |
| 8,197,443 B2 | 6/2012 | Sundar et al. |
| 9,186,172 B2 * | 11/2015 | Velez Rivera ..... A61B 17/3401 |

FOREIGN PATENT DOCUMENTS

WO 2018208367 A1 11/2018

* cited by examiner

*Primary Examiner* — Nathan R Price
*Assistant Examiner* — Justin L Zamory
(74) *Attorney, Agent, or Firm* — Johnson & Martin, P.A.; James David Johnson

(57) ABSTRACT

Provided is an epidural device configured to inhibit or substantially or completely prevent further progression of an epidural needle upon entry of the needle into the epidural space. When the needle is inserted into the ligamentum of the patient's back, the device may be pressurized with fluid using the resistance of the dense ligament to maintain pressure. This pressurization may lock a pushing mechanism in place relative to the needle such that the pushing mechanism can be used to advance the needle. Once the epidural space is reached, the fluid (e.g., saline or air) enters the epidural space, and the release of pressure may cause the trigger mechanism to disengage from the sliding pusher, allowing the pusher to slide along the body of the construct. The device thus may provide the ability to detect the epidural space using pressure loss while preventing the needle from advancing into the dura once the space is
(Continued)

reached. In a preferred aspect, the device may prevent premature triggering when there is a slow flow of fluid from the epidural needle into the surrounding tissue.

19 Claims, 20 Drawing Sheets

(51) Int. Cl.
*A61M 5/145* (2006.01)
*A61M 5/31* (2006.01)
*A61B 17/34* (2006.01)

(52) U.S. Cl.
CPC ........... *A61M 5/46* (2013.01); *A61B 17/3401* (2013.01); *A61M 2005/3128* (2013.01)

(58) Field of Classification Search
CPC ............ A61M 5/2066; A61M 5/31596; A61M 2005/3128; A61M 2005/3112; A61M 2005/3132; A61B 5/4896; A61B 17/3401
See application file for complete search history.

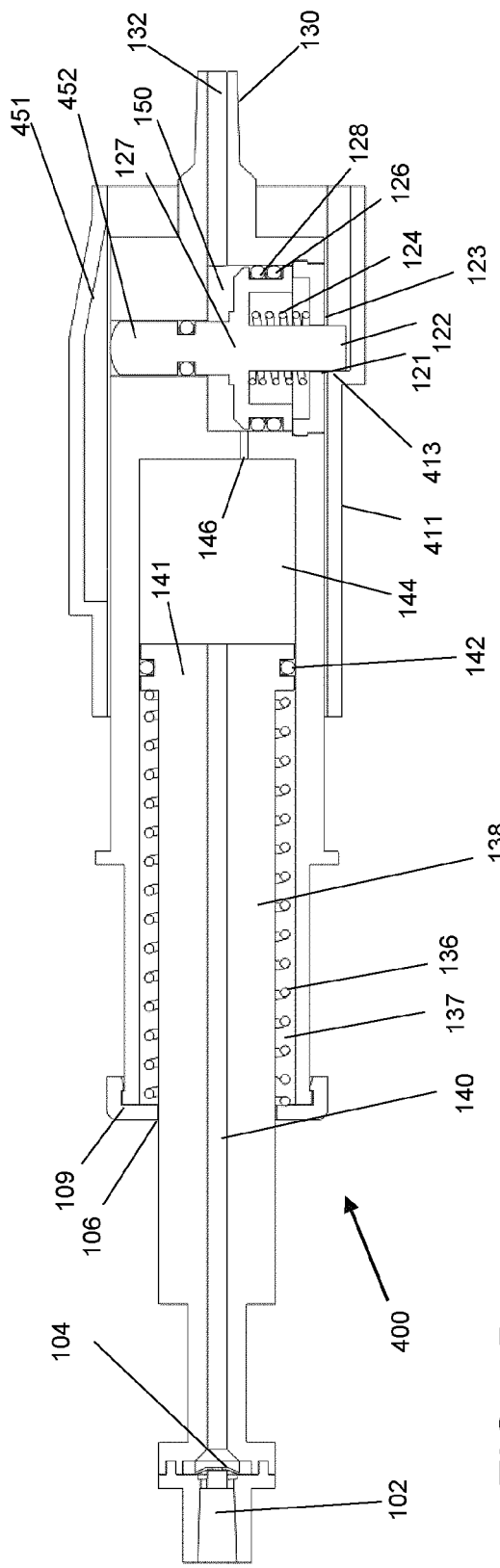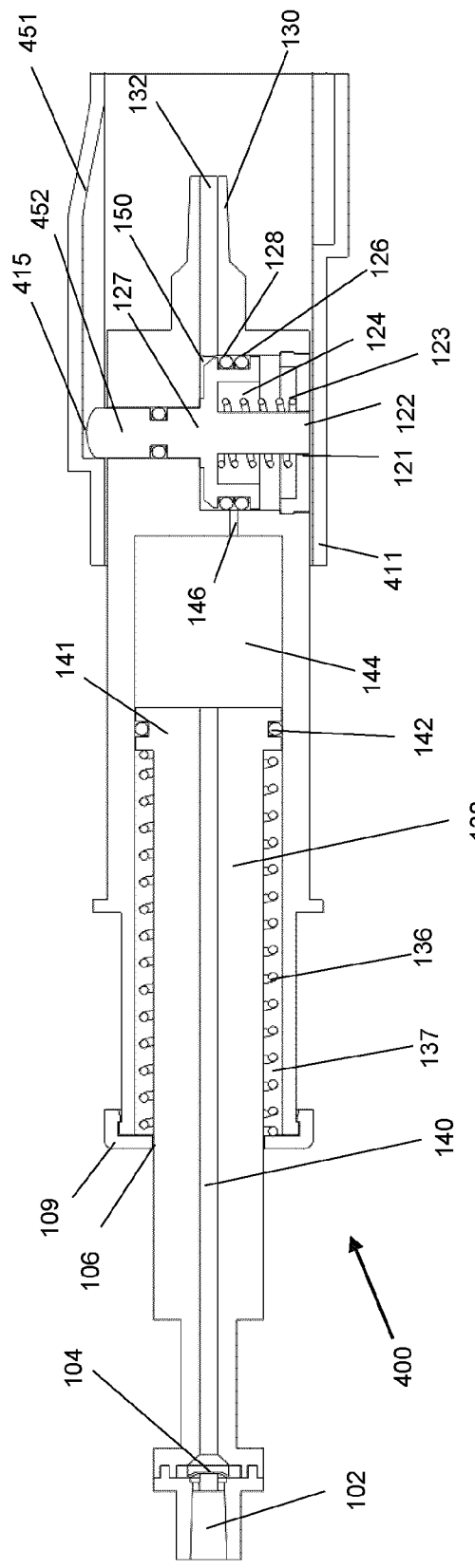
FIG. 4B
FIG. 4C

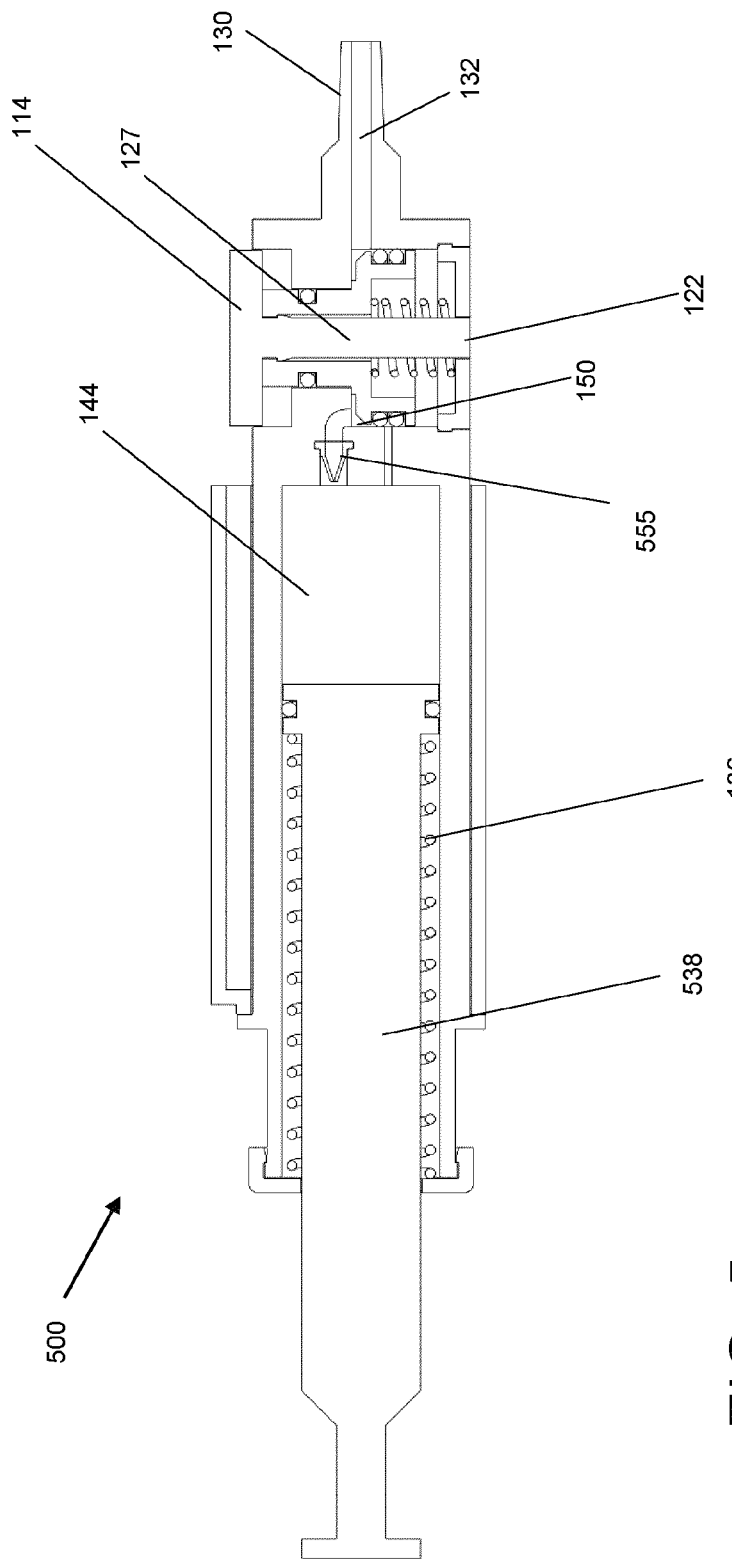

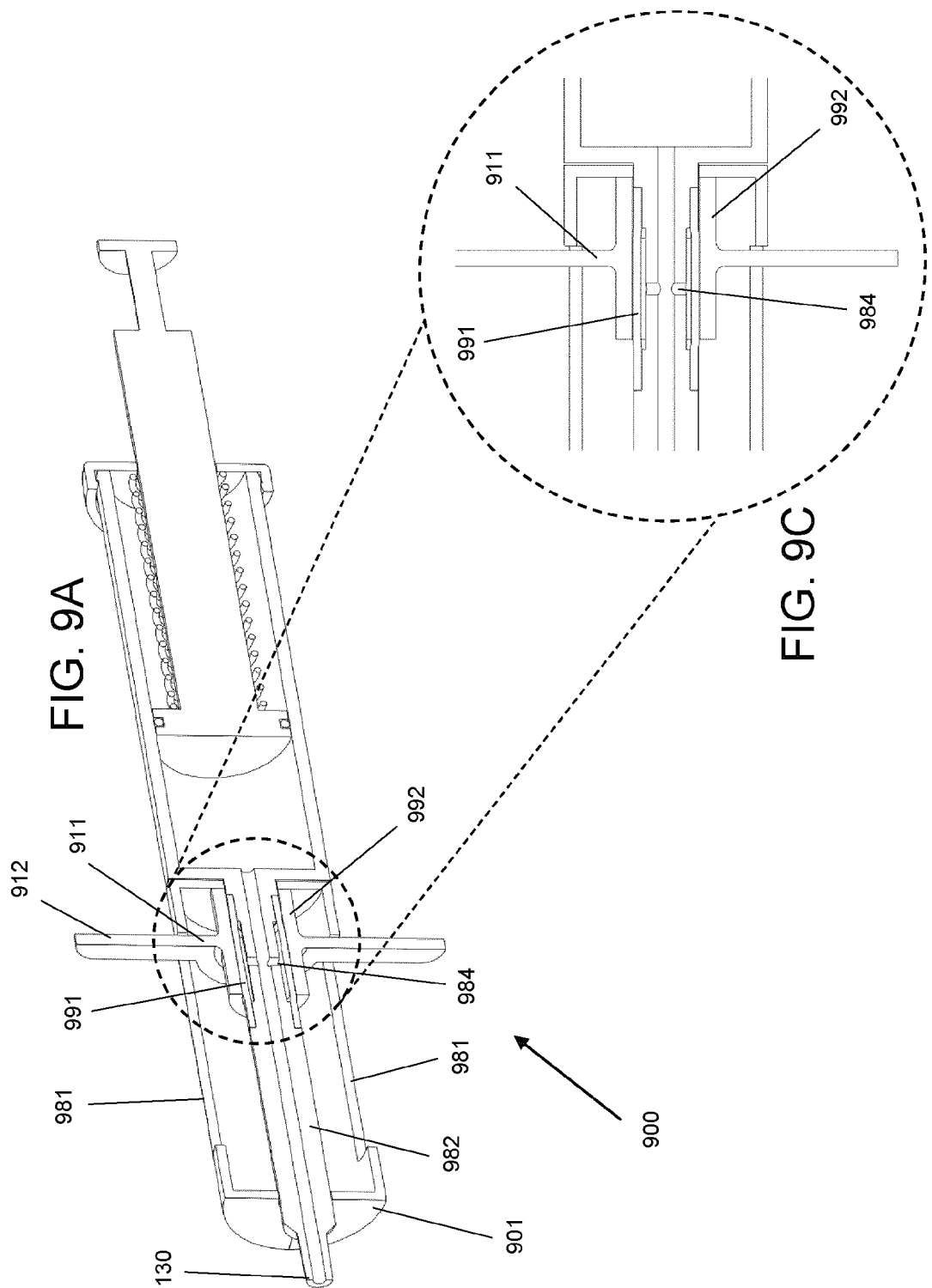

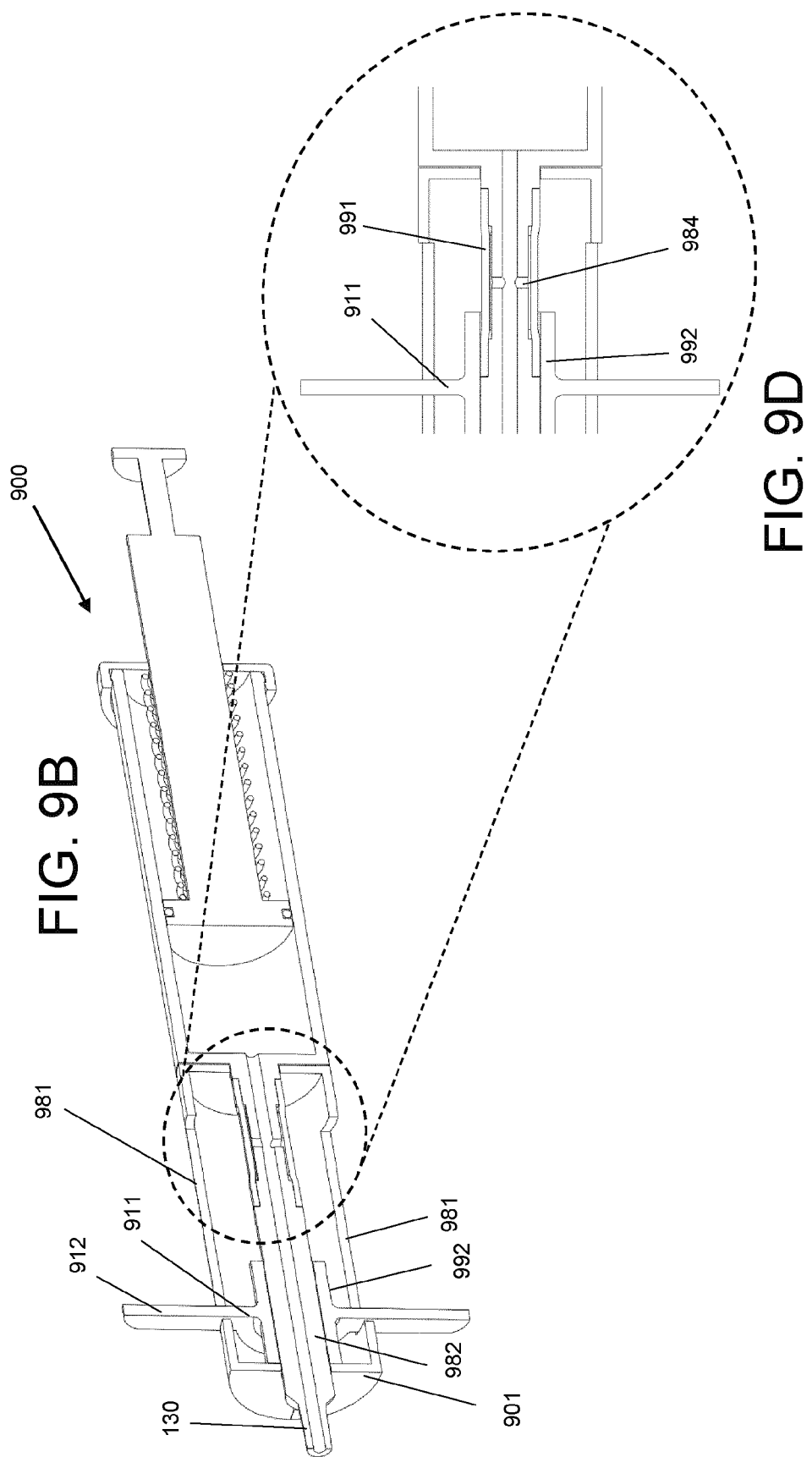

EPIDURAL DEVICE FOR DETECTION OF AND NEEDLE PLACEMENT IN EPIDURAL SPACE

CROSS REFERENCE TO RELATED APPLICATIONS

The present application is a continuation of International PCT Application No. PCT/CA2020/051147 filed on Aug. 21, 2020, which claims priority from U.S. Provisional Patent Application No. 63/039,951 filed on Jun. 16, 2020, and from U.S. Provisional Patent Application No. 62/891,313 filed on Aug. 24, 2019, the contents of which are all incorporated herein by reference in their entireties.

TECHNICAL FIELD

The following relates to devices used in epidural procedures, referred to herein as epidural devices. More particularly, the following relates to epidural devices for facilitating detection of and placement of an epidural needle in the epidural space.

BACKGROUND

Epidural anesthesia is widely used during labour/childbirth, lower limb and pelvic surgeries, and steroid injections for pain relief. Both single injection and catheter techniques can be used to inject medication into the epidural space. The ability to maintain continuous anesthesia after placement of an epidural catheter makes epidurals suitable for long duration surgeries and useful in the postoperative period for analgesia.

Typically, methods for placing the needle in the correct location rely on a loss of resistance to detect the epidural space (i.e., to determine when the epidural needle has entered the space). Once the needle tip is in the thick ligaments of the back, the anesthesiologist will apply constant or intermittent pressure to the plunger of an air or saline filled syringe. The anesthesiologist will commonly use a glass syringe or low resistance plastic syringe. Due to the dense and fibrous nature of the ligaments (supraspinous ligament, interspinous ligament and ligamentum flavum) leading up to the epidural space, saline or air will not be easily injected into the tissue and the syringe will maintain its pressurized state. The exact technique can vary, but generally, the epidural needle is advanced with one hand while pressure is maintained on the syringe plunger with the other hand. When the epidural needle tip enters the epidural space, the anesthesiologist senses the loss of pressure by depression of the syringe plunger. To confirm the location of the epidural space, additional saline can be injected into the space with ease. At this point, the syringe is removed and medication can be injected or a catheter can be fed through the needle. In an alternative, "incremental" method, the needle is advanced a millimeter or two, then the plunger is pressed to confirm the needle tip is still within the ligament. This occurs repeatedly until the plunger depresses with ease, releasing saline or air into the epidural space.

When using the incremental method, it is possible that between checks the needle can advance significantly through the epidural space and puncture the dura. The above-mentioned procedures rely upon the anesthesiologist to observe or sense the loss of pressure, process that information, and stop the forward progress of the needle without accidental additional forward motion of the needle. Poor technique, such as inadvertent angling of the plunger against the syringe walls, can create undesirable friction making it difficult to recognize the small changes in pressure needed to detect the epidural space. Furthermore, glass syringes typically have very low friction but will occasionally stick, creating a false negative signal for the doctor, resulting in the needle being advanced too far.

A risk of the epidural procedure is the accidental puncture of the dura. When the dura is punctured, the patient can suffer from post-dural puncture headache, spinal abscess, spinal hematoma, or permanent neurological damage in severe cases. Furthermore, when these complications arise, additional costs are incurred.

Current practice requires the anesthesiologist to observe the detection of the epidural space and simultaneously halt needle progression to prevent advancement that could cause dura puncture. Devices have been developed to provide a visual or auditory cue to alert the user of loss of pressure, thereby assisting the practitioner in detection of the epidural space. However, those devices are not configured to automatically inhibit or prevent further advancement of the needle once it has reached the epidural space.

In view of the foregoing, it is desirable to provide an improved epidural device.

SUMMARY

The following describes an epidural device configured to detect the entry of an epidural needle tip into the epidural space and to inhibit or prevent further progression upon entry. The device may be filled with fluid (e.g. saline or air), and connected to the epidural needle when the needle is inserted into a patient's back and the needle tip has been positioned in the ligamentum flavum. The device can be pressurized using the resistance of the dense ligament to prevent fluid flow from the needle. This pressurization may be used by a mechanism to lock a sliding pusher in place (relative to the body of the construct and the needle connected to it) such that the anesthetist can then use the pusher to advance the needle. Once the epidural space is reached, the fluid enters the epidural space, and the release of pressure may trigger the mechanism within the device, causing the pusher to disengage from the body of the construct. At this point if the sliding pusher is pushed, it may slide over the device without significant or any further advancement of the needle. The device may provide both the ability to detect the epidural space using pressure loss and to automatically substantially or completely prevent further progression of the needle once it has entered the epidural space.

In one aspect, there is provided an epidural device having an elongate body with a longitudinal axis, an inlet and an outlet, the epidural device comprising: a sleeve slidably disposed about an outer surface of the body; a first chamber defined in the body, the first chamber being configured to receive a fluid; a second chamber defined in the body, the second chamber being configured to convey the fluid to the outlet, the outlet being removably attachable to an epidural needle; a flow restrictor between the first and second chambers for providing fluid communication therebetween, wherein the flow restrictor has a smaller diameter than a diameter of the outlet; the first chamber having a first biasing mechanism positioned therein for pressurizing the first chamber; the second chamber having a piston provided therein, the piston being movable between: a primed position, where the piston is moved away from the flow restrictor, and the fluid can pass between first and second chambers; and a triggered (or unprimed) position, where the piston covers the flow restrictor, and the fluid can exit the second chamber via the outlet; wherein: in the primed position, the sleeve is engageable by an extension of the piston to inhibit the sleeve from moving axially toward the outlet; and in the triggered position, the sleeve is not engageable by the extension of the piston and the sleeve is movable axially toward the outlet.

In an implementation, the first chamber is configured to receive the fluid from the inlet, has an opening therein opposite the flow restrictor, and the device further comprises a plunger extending into the chamber through the opening, the plunger having: a flow port defined therein for providing fluid communication between the inlet and the first chamber; a distal end positioned within the first chamber; and a proximal end positioned outside of the chamber and being adapted to engage the inlet.

In another implementation, the first chamber has an opening therein opposite the flow restrictor, and the device further comprises a plunger extending into the chamber through the opening, the plunger having: a distal end positioned within the first chamber; and a proximal end positioned outside of the chamber.

In yet another implementation, the first biasing mechanism is a spring provided within the chamber and around the plunger intermediate the distal end thereof and the opening of the chamber.

In yet another implementation, a filling port for filling the first chamber extends between the first and second chambers, the filling port including a one-way valve to permit flow from the second chamber to the first chamber.

In yet another implementation, the flow restrictor is sized such that, when the device is in the primed position, at least some of the fluid can exit the second chamber through the outlet without triggering the device.

In yet another implementation, a second biasing mechanism is located within the second chamber, the second biasing mechanism being weaker than the first biasing mechanism.

In yet another implementation, the second biasing mechanism is a spring.

In yet another implementation, the piston includes a disk extending radially therefrom, the disk dividing the first chamber into trigger and reservoir chambers and having first and second annular surfaces in the trigger chamber and the reservoir chamber, respectively, the reservoir chamber being capable of fluid communication with the first chamber via a flow channel extending therebetween, wherein: when the device is in the primed position, the disk is positioned intermediate the flow channel and the flow restrictor and the trigger chamber can fluidly communicate with the first chamber and the outlet; and when the device is in the triggered position, the disk covers the flow restrictor and the trigger chamber cannot fluidly communicate with the first chamber.

In yet another implementation, the first annular surface has a greater surface area than a surface area of the second annular surface such that a force differential can be created between the trigger and reservoir chambers.

In yet another implementation, the piston includes, on an end thereof opposite the extension, a button pressable by a user in a direction toward the extension to prime the device.

In yet another implementation, the sleeve includes a protrusion extending therefrom toward the body of the device, the protrusion being configured to prime the device by depressing a button of the piston when the sleeve slides thereover, the button being attached to an end of the piston opposite the extension.

In another aspect, there is provided an epidural device having an elongate body with a longitudinal axis, an inlet and an outlet, the epidural device comprising: a sleeve slidably disposed about an outer surface of the body; a fluid passage defined in the body, the fluid passage being configured to receive a fluid from the inlet; a pressure chamber defined in the body, the chamber being configured to convey the fluid to the outlet, the outlet being removably attachable to an epidural needle; a flow restrictor between the fluid passage and the pressure chamber for providing fluid communication therebetween, the flow restrictor having a smaller diameter than a diameter of the outlet; the pressure chamber having a piston provided therein, the piston being movable between: a primed position, where the piston is moved away from the flow restrictor, and the fluid can pass between the fluid passage and the pressure chamber; and a triggered position, where the piston covers the flow restrictor, and the fluid can exit the pressure chamber via the outlet; wherein: in the primed position, the sleeve is engageable by an extension of the piston to inhibit the sleeve from moving axially toward the outlet; and in the triggered position, the sleeve is not engageable by the extension of the piston and the sleeve is movable axially toward the outlet.

In yet another aspect, there is provided an epidural device having an elongate body with a longitudinal axis, an inlet and an outlet, the epidural device comprising: a sleeve slidably disposed on an outer surface of the body; the body having a chamber defined therein for communicating a fluid between the inlet and the outlet, the outlet being removably attachable to an epidural needle; a biasing mechanism for pressurizing the chamber; a trigger mechanism for engaging the sleeve, the trigger mechanism being contained at least partially within the chamber and being movable between a first position and a second position by a decrease in pressure in the chamber; wherein: in the first position, the sleeve is engageable by the trigger mechanism to inhibit the sleeve from moving axially toward the outlet; and in the second position, the sleeve is not engageable by the trigger mechanism and the sleeve is movable axially toward the outlet.

In an implementation, the trigger mechanism comprises at least one piston having first and second ends, the first end being positioned in the chamber such that the first end can be acted on by the biasing mechanism, the second end extending radially outward through the body, wherein: in the first position, the second end protrudes radially from the body to an extent that the sleeve is engageable by the second end; and in the second position, the second end is positioned closer to the body than when the device is the first position, such that the sleeve is not engageable by the second end.

In another implementation, the trigger mechanism comprises an inflatable membrane that can be inflated by the biasing mechanism, wherein: in the first position, the inflatable membrane is inflated to an extent that the sleeve is engageable by the membrane; and in the second position, the inflatable membrane is deflated to an extent that the sleeve is not engageable by the membrane.

In yet another implementation, the trigger mechanism comprises a compliant component that can be expanded by the biasing mechanism, wherein: in the first position, the compliant component is expanded to an extent that the sleeve is engageable by the component; and in the second position, the compliant component is retracted to an extent that the sleeve is not engageable by the compliant component.

In yet another aspect, provided herein is a device for epidural procedures that can be filled with fluid and pressurized by means of an internal spring. The device further comprises: a sliding pusher on the external frame of the device, and a mechanism configured to have two positions. In one position, the sliding pusher is free to travel along the length of the device. In the other position, the pressure of the fluid holds the mechanism in place, and the sliding pusher is limited in movement as it interferes with the mechanism, allowing the user to advance the needle by means of pushing forward on the sliding pusher; when depressurized, such as when the needle tip enters the epidural space, the mechanism reverts to its other position and disengages from the sliding pusher, allowing the pusher to travel along the body of the device such that the user is unable to advance the needle further.

In an implementation, the mechanism consists of a piston that is movable vertically within the device and while in its first position may allow the sliding pusher to freely move; while in its second position it may inhibit the pusher component by way of one end of the piston engaging the pusher. The piston may be biased to be in its first position by means of a spring, and held in its second position by means of the fluid pressure within the device.

In an implementation, the sliding pusher component has flanges or wings which extend from its front end to provide a pushing surface when advancing the needle.

In another implementation, the flanges or wings are connected to the pusher by extensions, allowing the pushing surface to be closer to the patient, improving stability of the device and hand placement for the user.

In yet another implementation, the piston mechanism is movable into its second position by means of sliding the pusher forward (toward the patient). A ramp within the pusher may depress the piston mechanism as the pusher is advanced. When depressurized, the piston can move into a space within the pusher, allowing the pusher to slide freely.

In yet another implementation, the piston mechanism is movable into its second position by means of sliding the pusher back (away from the patient). A ramp within the pusher can depress the piston mechanism as the pusher is pulled back. When depressurized, the piston can move into a space within the pusher, allowing the pusher to slide freely.

In yet another implementation, the device may be filled with fluid by means of using a connector within the plunger of the device. A one-way valve within the plunger prevents fluid from exiting the chamber by the same path.

In yet another implementation, the device may be filled with fluid from the front of the device through a fluid path containing a one-way valve between the trigger mechanism and fluid reservoir.

In yet another implementation, the device may be filled with fluid from the front of the device by means of forcing the trigger mechanism into a position to allow fluid to pass and holding it in this position during the filling procedure.

In yet another implementation, the triggering mechanism does not contain a spring. In this aspect, the trigger piston may use differential forces from the pressurized on the two faces to drive the piston down or up, or hold it in place (down or up). The two faces may be of different sizes to enhance the differential forces. When depressurized, such as when entering the epidural space, the two faces of the piston mechanism may be subjected to differing forces, which can drive the piston up and allow the pusher to slide freely.

In yet another implementation, the trigger mechanism uses at least one and preferably two pins or two pistons which may interfere with the sliding pusher and in yet another implementation, the two pistons may provide equal and balanced force to the sliding pusher.

In another implementation, the device further comprises a flexible or inflatable membrane for engaging the sliding pusher when the membrane is pressurized. When depressurized, such as when entering the epidural space, the membrane may deflate and allow the sliding pusher to slide freely.

In yet another implementation, the device further comprises a compliant or flexible mechanism for engaging the sliding pusher when the mechanism is pressurized. When depressurized, such as when entering the epidural space, the compliant mechanism may retract and disengage from the sliding pusher, allowing the pusher to slide freely.

BRIEF DESCRIPTION OF THE DRAWINGS

Embodiments will now be described with reference to the appended drawings wherein:

FIG. 3A shows the device in its unprimed state. FIG. 3B shows the device in its primed state. FIG. 3C shows the device in its triggered state.

FIGS. 4A-4C illustrate cross-sectional views of an embodiment of the device in which the trigger mechanism is engageable by a ramp within the sliding pusher by pulling the pusher away from the needle end of the device. FIG. 4A shows the device in its unprimed state. FIG. 4B shows the device in its primed state. FIG. 4C shows the device in its triggered state.

FIG. 5 illustrates a cross-sectional view of an embodiment of the device in which a one-way valve within the device may permit filling of the reservoir chamber through the front of the device.

FIG. 6A shows the device in its unprimed state. FIG. 6B shows the device in its primed state. FIG. 6C shows the device in its triggered state.

FIG. 7A shows the device in its unprimed state. FIG. 7B shows the device in its primed state. FIG. 7C shows the device in its triggered state.

FIG. 8A shows the device in its primed state. FIG. 8B shows the device in its triggered state.

FIGS. 9A to 9D illustrate an embodiment of the device which uses a compliant or flexure mechanism and trigger ring to engage the sliding pusher with the body of the device. FIG. 9A shows the device in its primed state. FIG. 9B shows the device in its triggered state. The inset, FIG. 9C, shows a zoomed-in view of the compliant mechanism engaged with the sliding pusher in its primed state. The inset, FIG. 9D, shows a zoomed-in view of the compliant mechanism retracted, allowing the sliding pusher to move freely, in its triggered state.

DETAILED DESCRIPTION

One or more of the terms "vertical", "vertically", "horizontal", "horizontally", "top", "bottom", "upwardly", "downwardly", "upper", "lower", "right", "left", "forward" and "backward" are used throughout this specification. It will be understood that these terms are not intended to be limiting. These terms are used for convenience and to aid in describing the features herein, for instance as illustrated in the accompanying drawings.

The term "fluid" as used herein with respect to operation of the epidural device refers to a liquid or gas, e.g., saline or air, for filling and pressurizing the device.

An object of the following is to provide an epidural device capable of detecting the entry of the needle into the epidural space and simultaneously inhibiting or substantially preventing further forward motion of the needle. Such functionality may reduce the likelihood of dural puncture which can occur while carrying out the conventional loss of resistance technique. In a preferred aspect, the device is configured to prevent premature triggering when there is a slow flow of fluid from the epidural needle into surrounding tissue.

Loss of Pressure Designs

The epidural devices described with reference to FIGS. 1-5 include trigger mechanisms that rely on differential forces between a spring force and a force from chamber pressure in the trigger barrel. These devices are configurable between "primed" and "triggered" (i.e., unprimed) positions or states. The devices can be primed (i.e., shifted from unprimed to primed) manually by a user, such as a physician, when attached to a needle which is positioned in a patient's back, and subsequently automatically triggered upon entry of the epidural needle into the epidural space. The unprimed (triggered) state is the default state for the epidural devices. Step-by-step operation of these devices will be described following the below description of their structure.

Figure 1A:
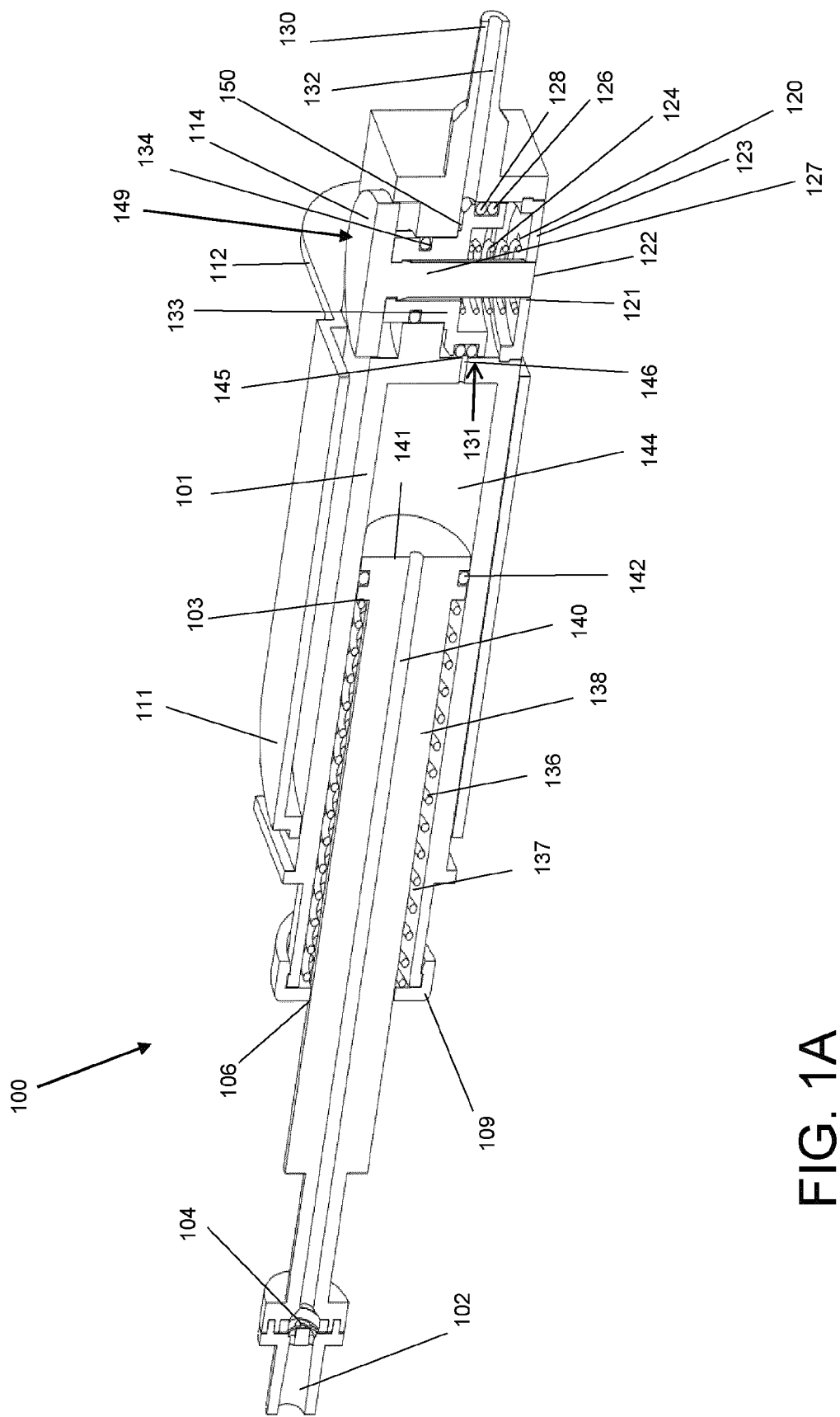
FIG. 1A illustrates a cross-sectional side view of an epidural device showing the internal workings of the reservoir, plunger, trigger mechanism, and springs.

FIG. 1A illustrates an epidural device 100 comprising a syringe body 101 having a first, or open end 106 and a second, or needle connector end 130. The syringe body 101 can have a substantially uniform shape with a rectangular cross-section, as shown in FIG. 1A. The syringe body 101 may be shaped differently. For example, the body 101 may be an elongate body having a different (i.e., not rectangular) polygonal cross-section, e.g., hexagonal. In FIG. 1A, the epidural device 100 is shown in the unprimed position, with the reservoir partially filled with a fluid (not shown). The body 101 may include a reservoir chamber 144 shaped to slidably receive and retain a plunger 138 for filling and pressurizing the reservoir chamber 144. The reservoir plunger 138 can be movable parallel to a longitudinal axis of a filling port 140 extending through the plunger 138. The body 101 may include a fluid flow restrictor 146 extending between the reservoir chamber 144 and a trigger barrel 131. The restrictor 146 may induce a pressure drop between the reservoir chamber 144 and the trigger barrel 131 when fluid flow occurs therebetween. The diameter of the restrictor 146 may be smaller than that of the exit port 132. In the unprimed position shown in FIG. 1A, fluid flow between the reservoir chamber 144 and the trigger barrel 131 may be blocked by a pair of disk seals 126 and 128. The device further comprises a sleeve, or pusher 111 by which a user can advance an epidural needle 147 (see FIG. 1B) connected to the needle connector end 130. The pusher 111 can be slidably disposed over the syringe body 101. The pusher 111 can optionally have external flanges or wings 112, and/or texture or shape for ergonomic purposes. As discussed further below, the pusher 111 can be configured to interact with a trigger mechanism of the device 100.

The filling port 140 may provide fluid communication between a filling connector 102 and the reservoir chamber 144. A one-way valve 104 is provided within the filling port 140 to inhibit or substantially prevent backflow and to allow the reservoir chamber 144 to be filled from the back end, thereby obviating the need to fill the reservoir chamber 144 from the needle connector end 130 through an exit port 132, which may require having to manually hold the device in the primed position during filling. A widened portion 141 of the plunger 138 may include a seal 142 and an annular shoulder 103.

The device 100 further comprises a trigger mechanism 149 designed to respond to pressure of the fluid in the trigger barrel 131, which in turn is affected by the pressure of the fluid in the reservoir chamber 144. A biasing mechanism, particularly a reservoir spring 136 is disposed around the plunger 138 and in a space 137 formed between a reservoir cap 109, which may cover the open end 106, and an annular shoulder 103. Other biasing mechanisms such as flexible rubber (e.g. elastic band) or compressed air can be implemented instead of a spring. The reservoir spring 136, anchored against the reservoir cap 106, can bias the reservoir plunger 138 in a direction toward the restrictor 146 and thereby pressurize the fluid within the reservoir chamber 144.

The trigger mechanism 149 may comprise a trigger piston 133 having a trigger piston core 127 therein. The trigger piston 133 may be provided within the trigger barrel 131, and a first, or lower disk seal 126 and a second, or upper disk seal 128 may be provided on the outer circumference of the trigger piston 133. The trigger piston core 127 can be directly connected to the trigger piston 133 such that these components can move together in unison. A third circumferential priming seal 134 may be disposed around the trigger piston 133. A space defined by the priming seal 134, the disk seal 128 and between a wall 145 of the trigger barrel and the trigger piston 133, may be referred to as a trigger chamber 150. The trigger piston core 127 may have a priming, or trigger button 114 and a trigger pin 122 extending from upper and lower surfaces, respectively, of the trigger barrel 131. The trigger piston 133 is slidable within the trigger barrel 131. The priming seal 134, and the disk seal 128 may substantially prevent leaking of fluid from the trigger chamber 150 out of the top and bottom ends thereof. The two disk seals 126 and 128 of the trigger piston 133 may create sliding seals between the trigger barrel wall 145 and the trigger piston 133. The priming seal 134 may create a sliding seal between the trigger piston 133 and a narrower section of the trigger barrel wall 145. The trigger 123 cap may connect to and close an open end of the trigger barrel 131.

Figure 1B:
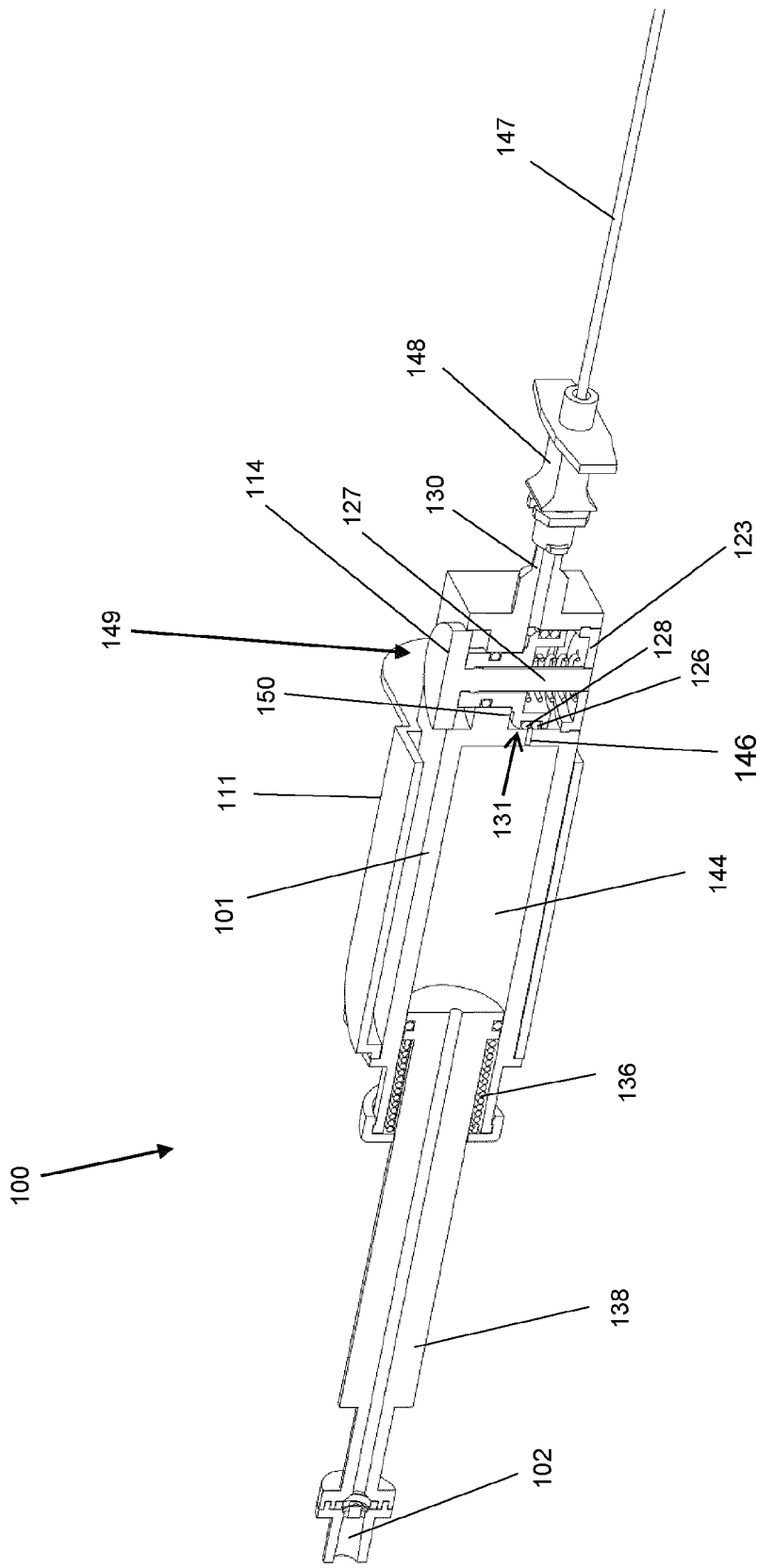
FIG. 1B illustrates a cross-sectional side view of the device shown in FIG. 1A, in the filled and unprimed state, attached to an epidural needle.

The exit port 132 may be provided at the "forward" end (i.e., near the needle connector end 130 of the device 100) of the trigger barrel 131. The exit port 132 leads to the needle connector end 130 which can be removably attachable to a needle connector 148 (FIG. 1B) for connecting to an epidural needle 147 (FIG. 1B). The exit port 132 can allow fluid to exit the trigger barrel 131, and ultimately to exit the device 100 through the needle 147.

A trigger spring 124 can be positioned around and concentric with the trigger pin 122 and may bias the trigger piston 133 away from the trigger cap 123. The trigger cap 123 may include a trigger pin hole 121 and a vent hole 120. The vent hole 120 can be optional as the trigger pin hole 121 may double as a vent hole. The vent hole 120 in the trigger cap 123 may substantially prevent air that is stuck between the trigger cap 123, trigger barrel 131, and trigger piston 133 from impeding the sliding motion of the trigger mechanism 149. As such, the trigger piston core 127 and the trigger pin 122 can fit inside the trigger piston 133 and the trigger barrel 131 such that the trigger pin 122 can slide vertically through the trigger pin hole 121.

FIGS. 1B-1G illustrate the epidural device 100 in various states or alternative views. For clarity, relative to FIG. 1A, fewer elements are labeled in FIGS. 1B-1G. FIG. 1B illustrates the device 100 in the unprimed, filled state, wherein the reservoir plunger 138 is held away from the restrictor 146 by fluid in the reservoir chamber 144. As shown, in the filled state, the reservoir spring 136 is at least partially compressed and thus may pressurize the fluid within the reservoir chamber 144. In this state, fluid communication between the trigger chamber 150 and the reservoir chamber 144 can be inhibited and preferably substantially prevented by the upper disk seal 128. The lower disk seal 126 may prevent fluid from leaking out the bottom of the trigger barrel 131 through the trigger cap 123.

Figure 1C:
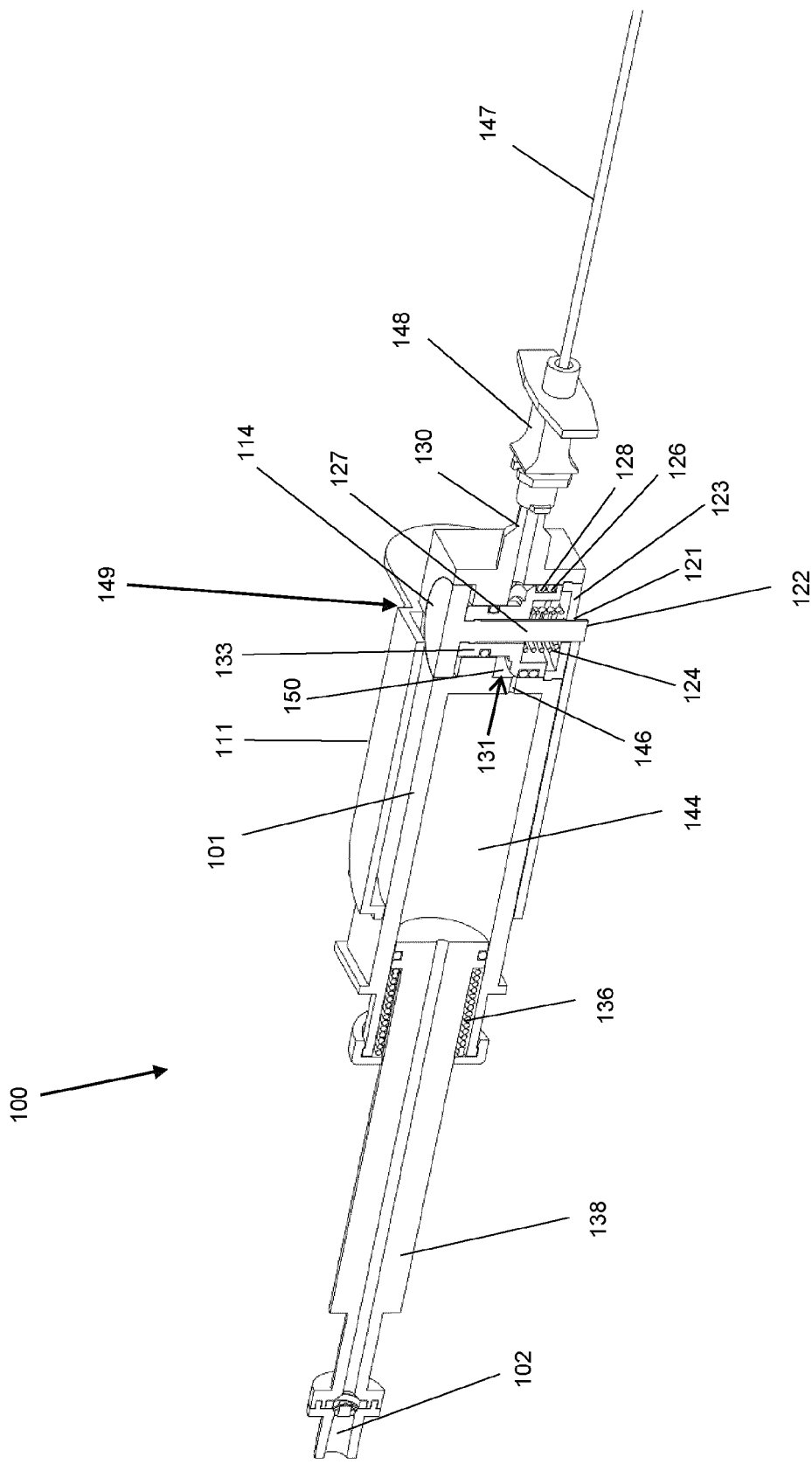
FIG. 1C illustrates a cross-sectional side view of the device shown in FIG. 1A, in the filled and primed state, attached to an epidural needle.

FIG. 1C shows the device 100 in the filled, primed position, wherein the button 114 has been manually pressed down, moving the trigger piston 133 against the trigger cap 123, thereby shifting the trigger pin 122 such that same extends out of the trigger pin hole 121. When the device is in the primed position, the axial movement of the sliding pusher 111 can be limited by the trigger pin 122. More particularly, when moved advanced axially toward the needle connecter end 130, the pusher 111 will, at a certain point, abut the trigger pin 122, thereby substantially preventing further sliding of the pusher 111 with respect to the body 101. When the pusher 111 abuts the trigger pin 122, most or substantially all force can be transferred from the pusher 111 through the device 100 to the epidural needle 147 (see below discussion regarding operation).

Figure 1D:
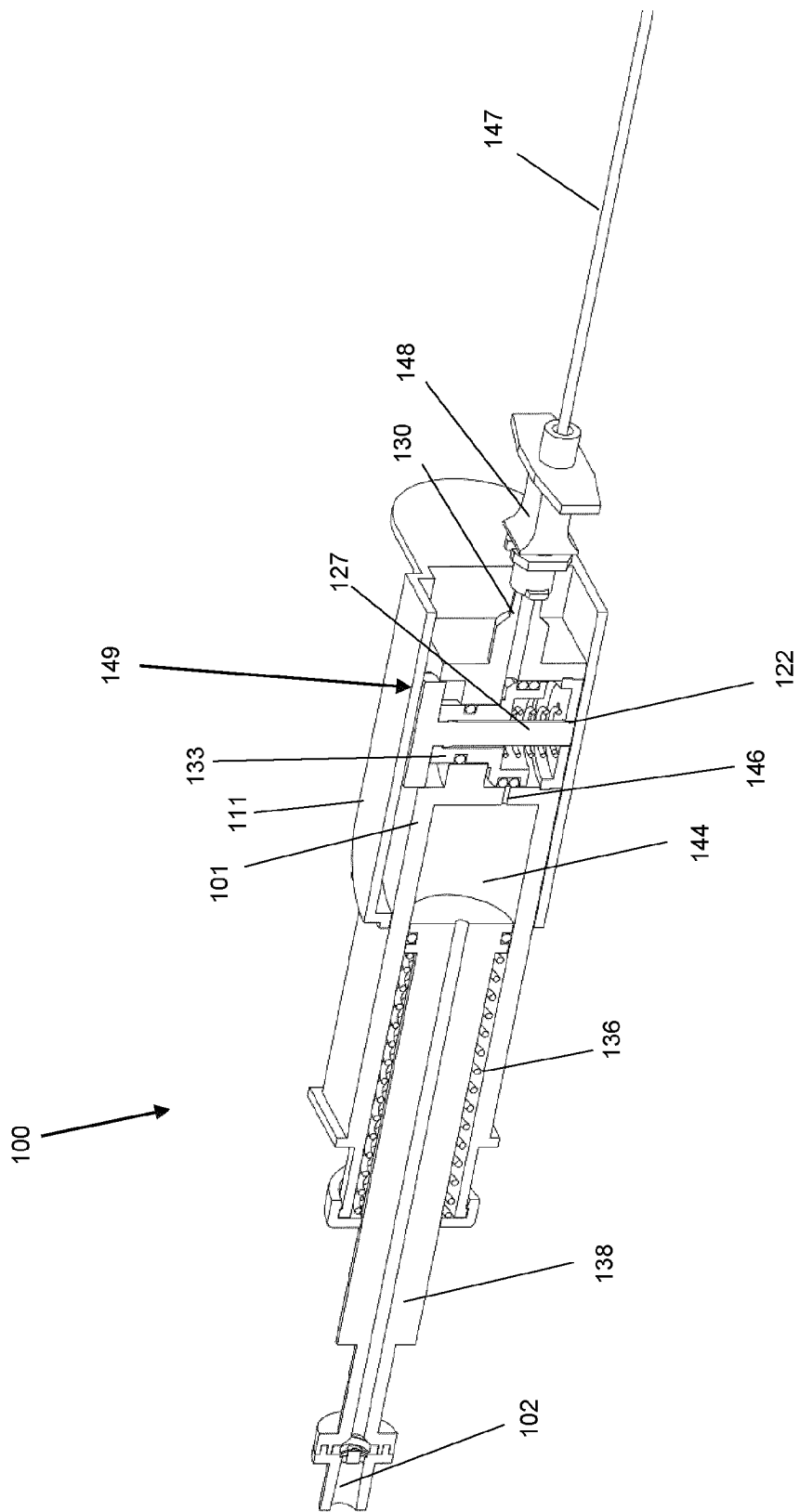
FIG. 1D illustrates a cross-sectional side view of the device shown in FIG. 1A, in the partially filled and triggered state, (such as after entering the epidural space), attached to an epidural needle.

FIG. 1D shows the device 100 in the partially filled, triggered position, as would be expected after the epidural needle 147 has become "unblocked" by entering the epidural space, resulting in pressure drop across the restrictor 146 and subsequent upward movement of the trigger piston 133 to return to the unprimed state. In this triggered state, the trigger pin 122 does not prevent sliding of the pusher 111 and preferably does not at all impede sliding of the pusher. Thus, force transfer (in the axial direction), with the exception of frictional force between the pusher 111 and body 101, may be substantially reduced and preferably prevented between the pusher 111 and the needle 147, thereby preventing further advancement of the needle 147 into the epidural space.

Figure 1E:
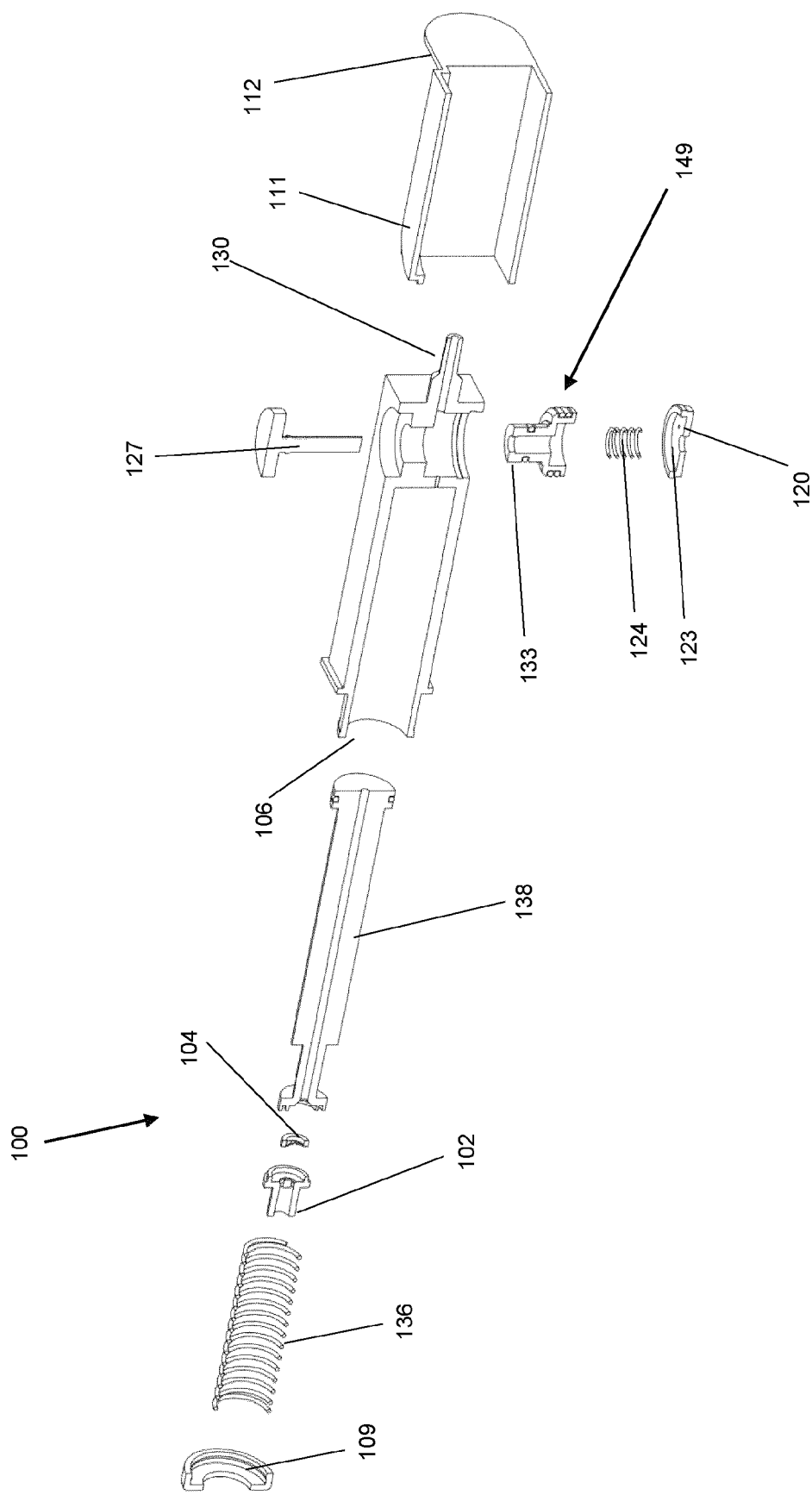
FIG. 1E illustrates a cross-sectional exploded view of the device shown in FIGS. 1A-1D.
Figure 1F:
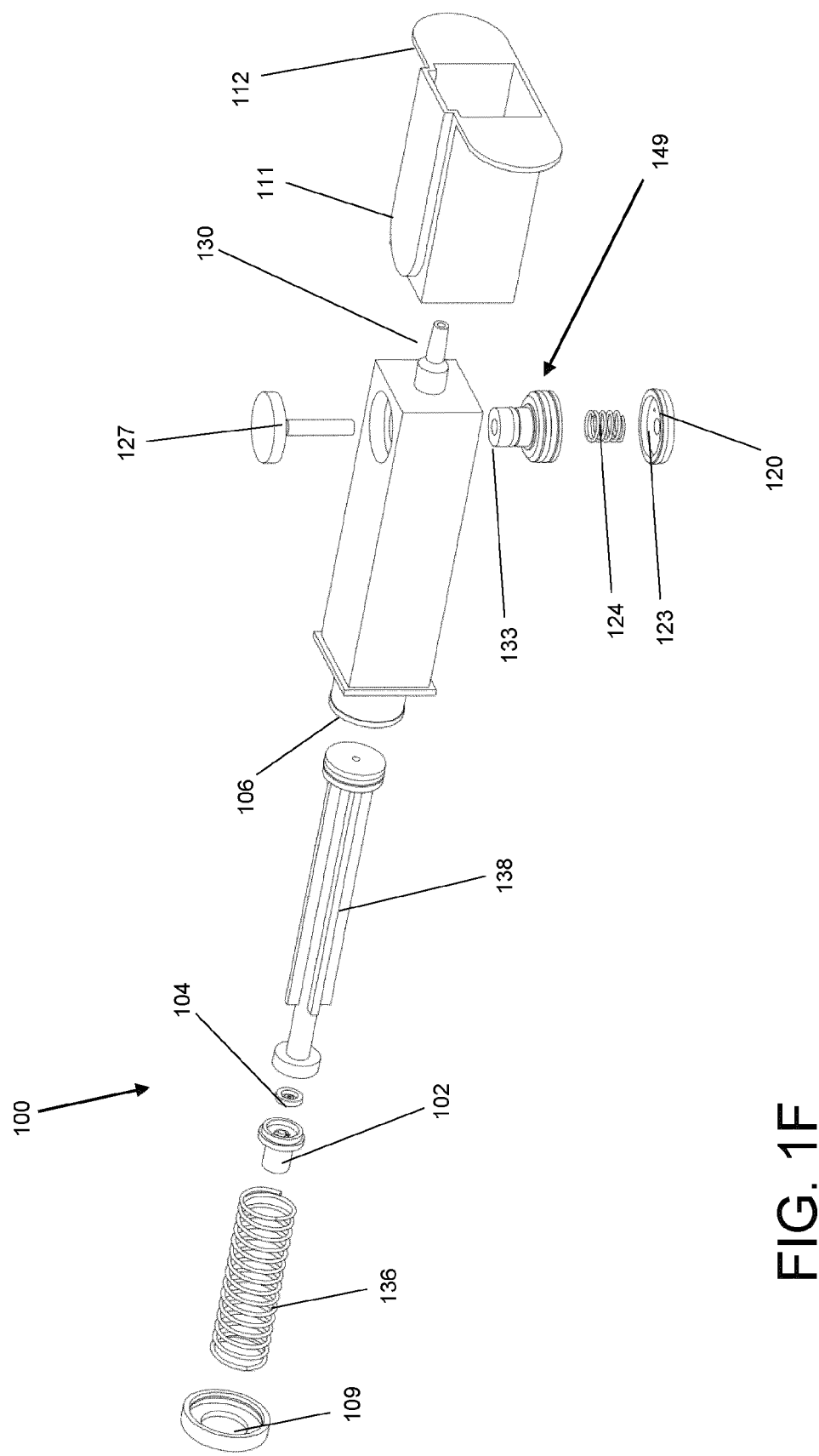
FIG. 1F illustrates an exploded view of the device shown in FIGS. 1A-1D.

FIG. 1E and FIG. 1F illustrates exploded views of the component part of device 100, with FIG. 1E showing a cross-sectional exploded view.

Figure 1G:
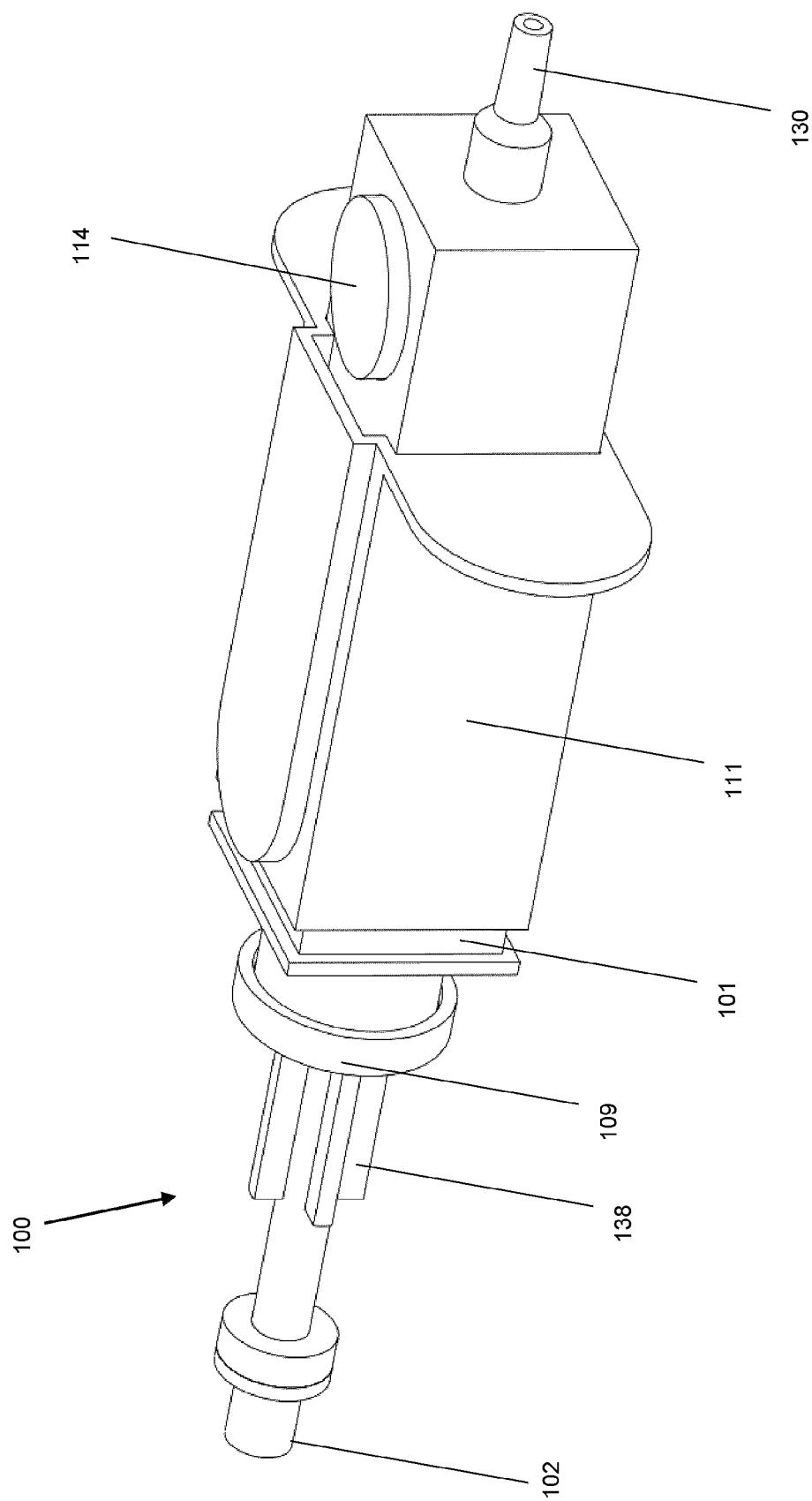
FIG. 1G illustrates an annotated isometric view of the device shown in FIGS. 1A-1F.

FIG. 1G illustrates an isometric view of the assembled device 100.

The devices depicted in FIGS. 2-5 are functionally similar to the device 100 shown in FIG. 1. Thus, similar elements will retain the same reference numbers.

Figure 2:
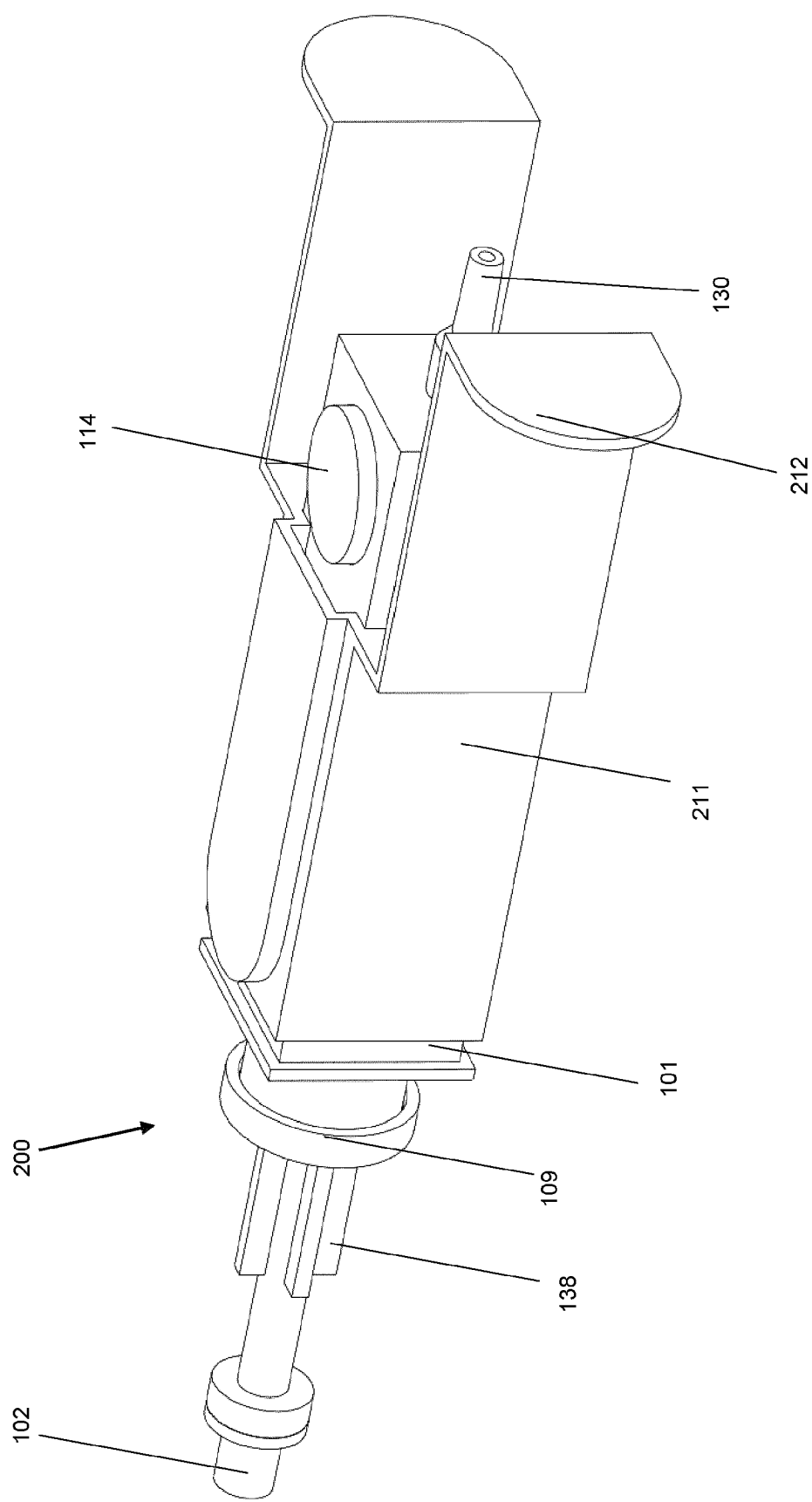
FIG. 2 illustrates an annotated isometric view of a device similar to that shown in FIG. 1, with flanges for the wings of the pusher that are extended toward the front of the device.

FIG. 2 illustrates an isometric view of a similar epidural device 200 in the assembled state, wherein the pusher 211 has extended wings 212. In this configuration, the wings are closely aligned with the needle connector (148, not shown in this image), and may provide improved handling for the user.

Figure 3A:
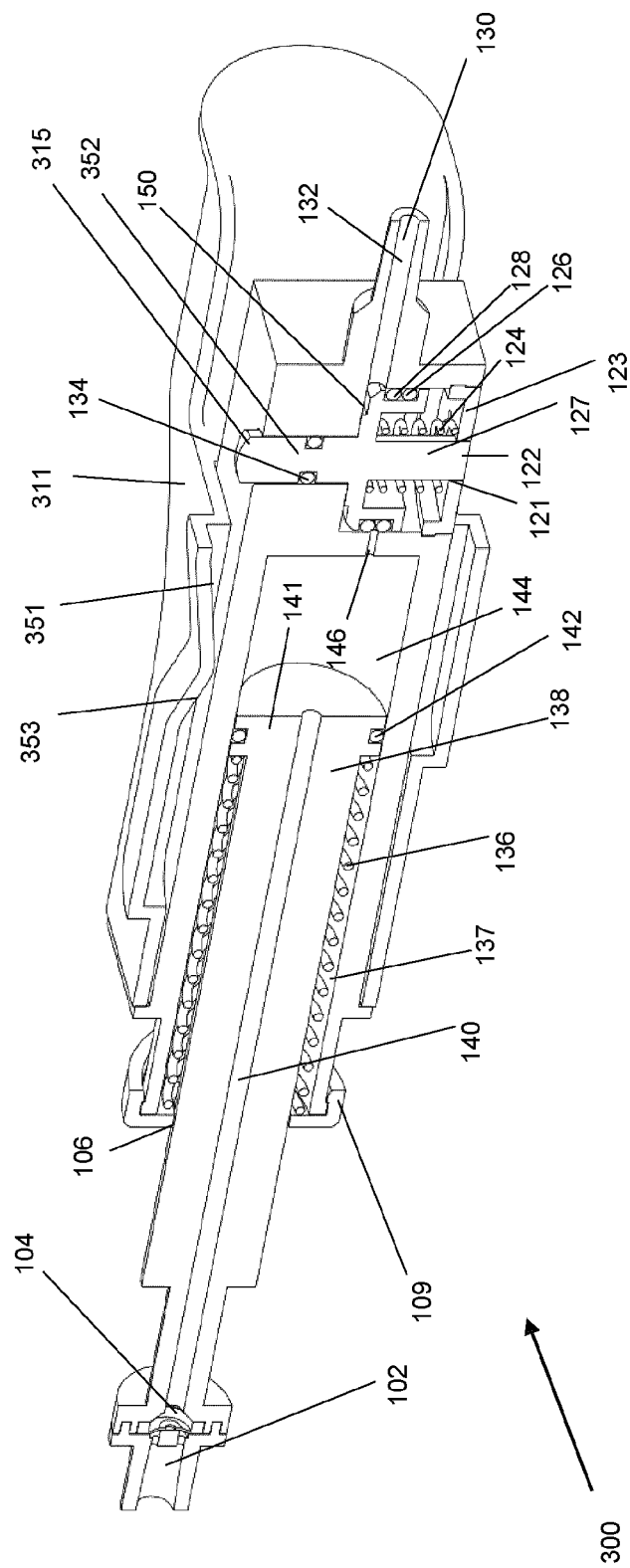
FIGS. 3A-3C illustrate isometric cross-sectional views of an embodiment of the device in which the trigger mechanism is engageable by a ramp within the sliding pusher by sliding the pusher toward the needle end of the device.
Figure 3B:
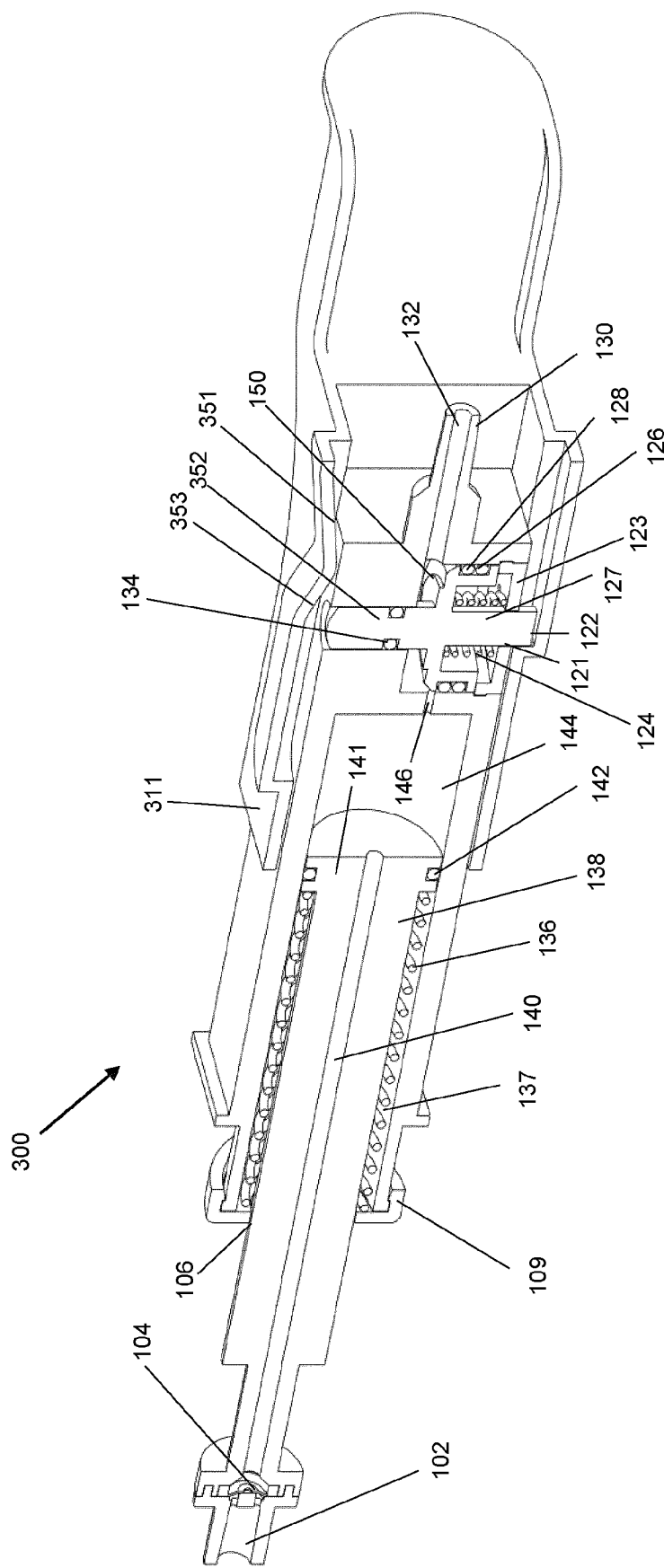
Figure 3C:
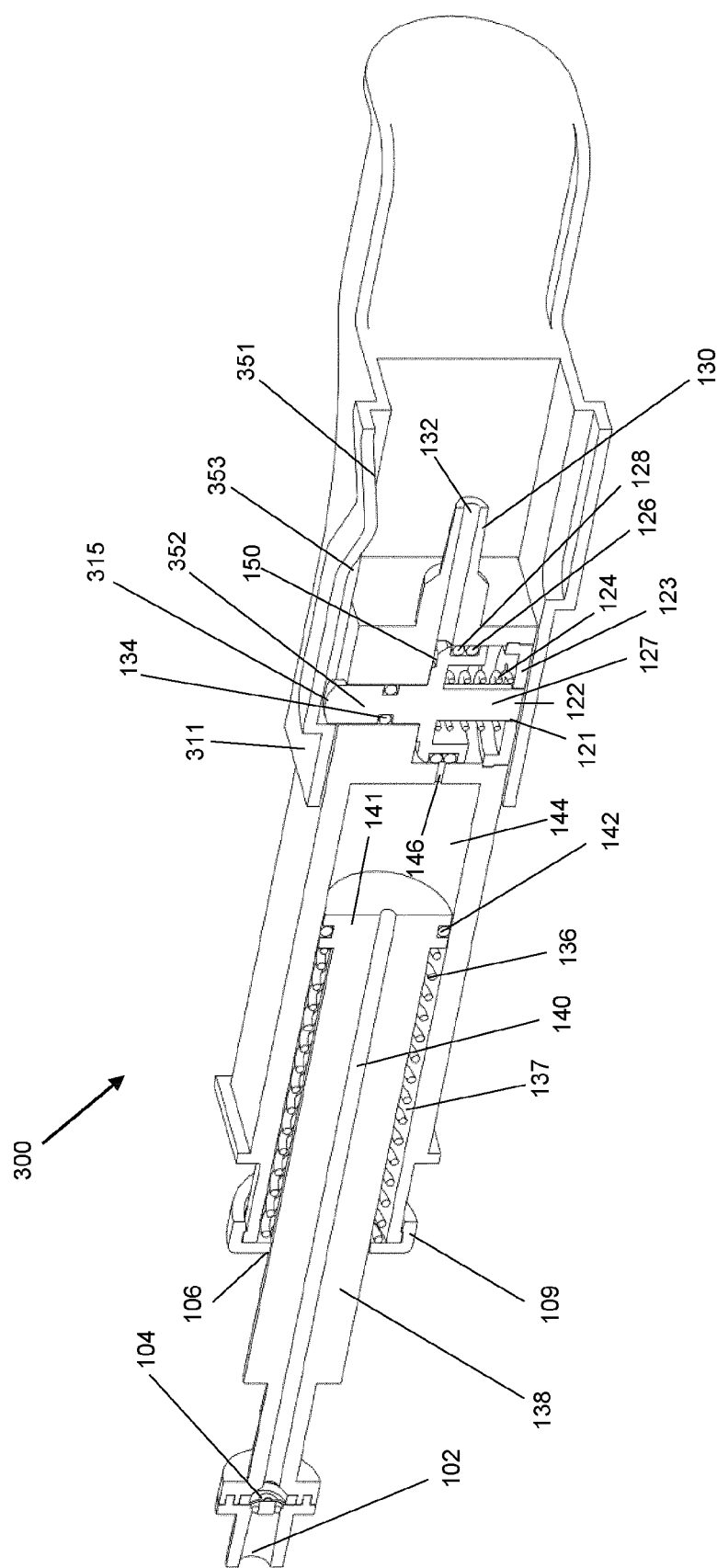

FIG. 3 illustrates an epidural device 300 similar to device 100, but the device 300 can be primed differently in that the pusher can be used to depress the trigger piston to prime the device. FIG. 3A shows the device 300 in the unprimed position. The device 300 comprises a trigger piston 352 which is a single component in this example embodiment, and a pusher 311 having a priming ramp 351 and a reset ramp 353. The trigger piston 352 may function similarly to the trigger mechanism 149 above. The device 300 can be primed by sliding the pusher 311 forward, whereby a priming ramp 351 may engage with a priming button 315 of the trigger piston 352 and thereby push it down into the primed state, shown in FIG. 3B. As described above, the trigger pin 122 extends out of the trigger hole 121 and may prevent forward sliding of the pusher 311, thus transferring force from the pusher 311 through the device 300 to the epidural needle 147 (not shown). FIG. 3C shows the device in the triggered state, where the trigger piston 352 is permitted to move upwards and thus the trigger pin 122 is not engaged with the pusher 311, allowing the pusher 311 to slide forward without significantly or preferably at all advancing the needle 147. The device can be reset by sliding the pusher back across the trigger mechanism, utilizing the reset ramp 353 to manipulate the trigger piston 352 as needed.

Figure 4A:
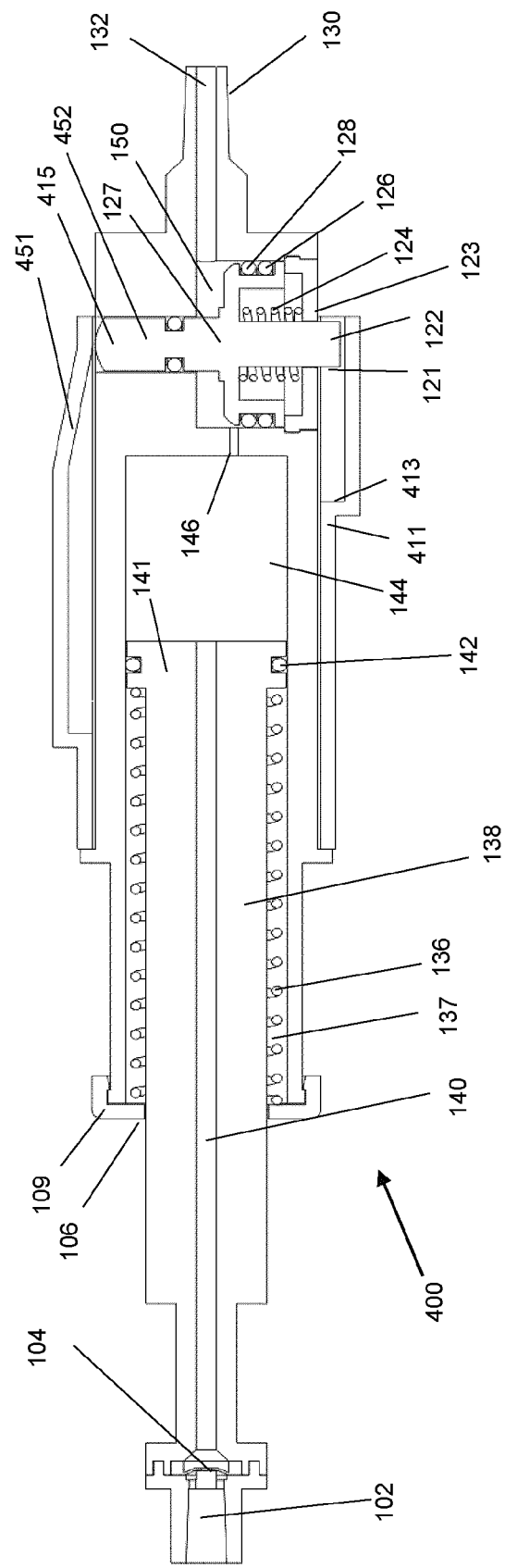

FIGS. 4A-4C illustrate another epidural device 400 that is similar to devices 100 and 300. The device 400 comprises a pusher 411 that can be used to prime the trigger piston 452, in this case by pulling the sliding pusher 411 away from the needle connector end 130. FIG. 4A shows the device in the primed position, at the moment that the sliding pusher 411 has been pulled back and the priming ramp 451 has engaged a priming button 415 of the trigger piston 452 to push it down into the primed state thereby causing the trigger pin 122 to extend outwardly from the trigger pin hole 121 such that the trigger pin 122 can abut a shoulder 413 defined in the pusher 411. FIG. 4B is also in the primed state, but with the sliding pusher 411 pushed forward to the extent that the trigger pin 122 engages the pusher 411 at the shoulder 413 such that further movement of the pusher 411 toward the needle connector end 130 is inhibited or prevented. In this state, a majority of a pushing force can be transferred from the pusher 411 through the device 400 to the epidural needle 147 (not shown), thereby enabling advancement of the needle 147 toward the epidural space. FIG. 4C shows the device in the triggered state, where a decrease in pressure resulting from entry of the needle 147 into the epidural space has caused the pin 452 to move upwardly such that the trigger pin 122 may no longer engage the shoulder 413. As a result, the pusher 411 may slide further toward the needle connector end 130 and advancement of the needle 147 is thus inhibited or prevented. In FIG. 4C, the pusher 411 has been moved toward the needle connector 132 to its full extent.

The devices described above each include a reservoir chamber that can be filled with a fluid which can be pressurized by a biasing mechanism in the reservoir chamber. A reservoir chamber may not be needed to pressurize the fluid before the restrictor. Instead, for example, the filling port 140 could extend from the valve 104 to the restrictor 146 and be integrated physically with the body 101 (i.e., the port 140 could extend through a length of the body 101 to the restrictor 146). The filling port 140 could be pressurized by, for example, being connected to a pressurized fluid line (i.e., leading to the 1-way valve 104). This could obviate the need for a reservoir chamber 144.

FIG. 5 illustrates another epidural device 500 that is similar to device 100. In this version, the reservoir chamber is filled through the port 132 at the front of the device, instead of through the filling port 140 as is described with respect to FIG. 1A. The device 500 thus may include a plunger 538 that does not have such a filling port 140 defined therein. It follows that the one-way valve 104 and the filling connector 102 are not needed in the device 500. Fluid may enter the reservoir 144 through the trigger chamber 150 and through a one-way valve 555, by means of pulling back on the reservoir plunger 538. Functionally, this device is otherwise similar to the device 100.

Differential Pressure Design

Figure 6A:
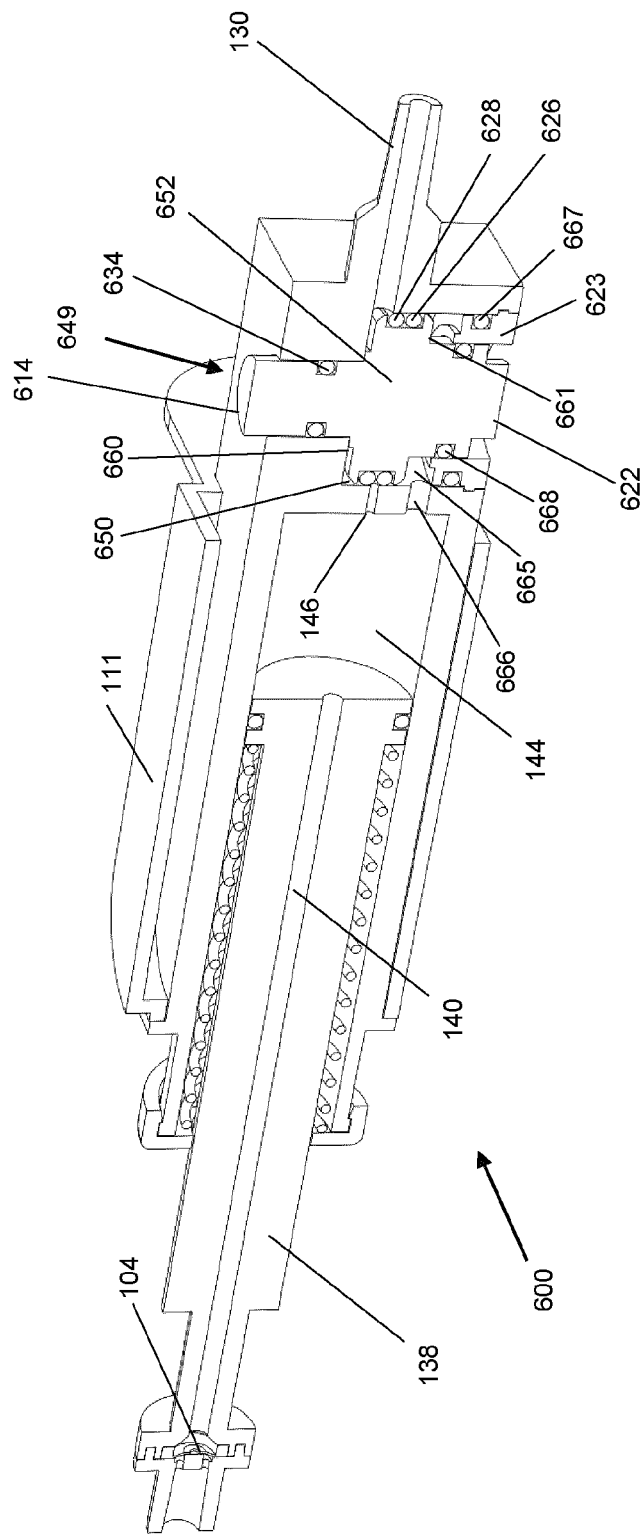
FIGS. 6A-6C illustrate an isometric cross-sectional view of an embodiment of the device in which differential pressure may drive the trigger piston mechanism up and down.
Figure 6B:
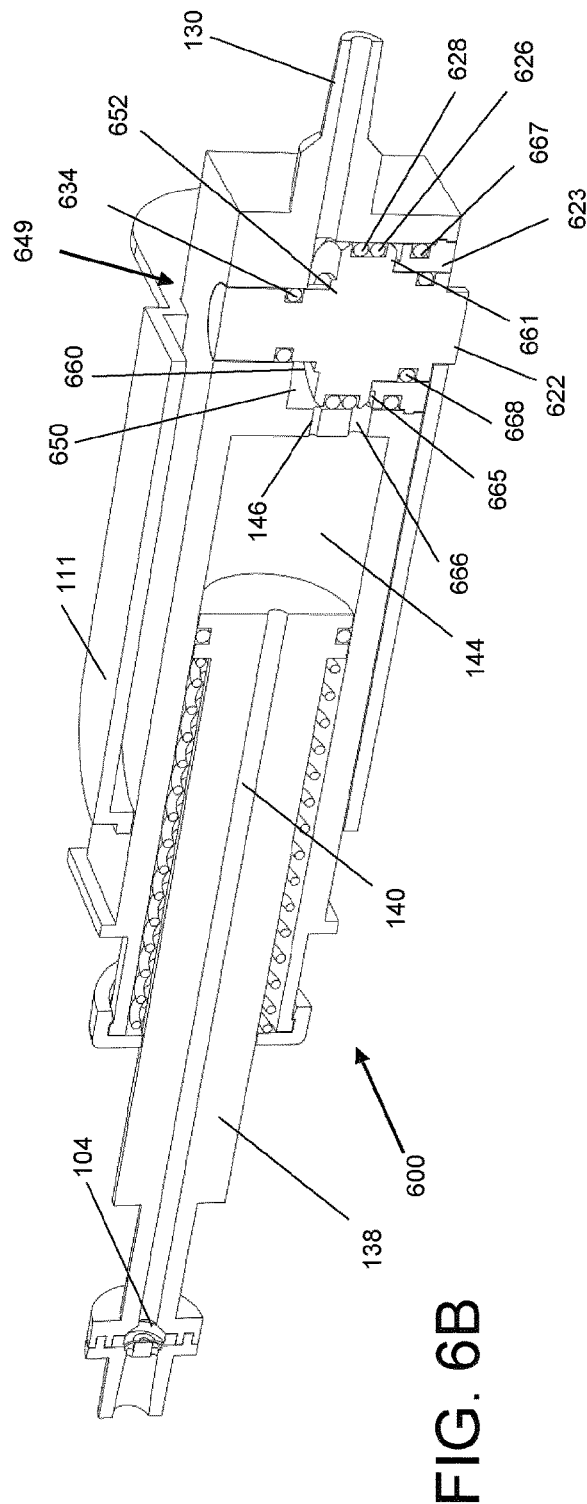
Figure 6C:
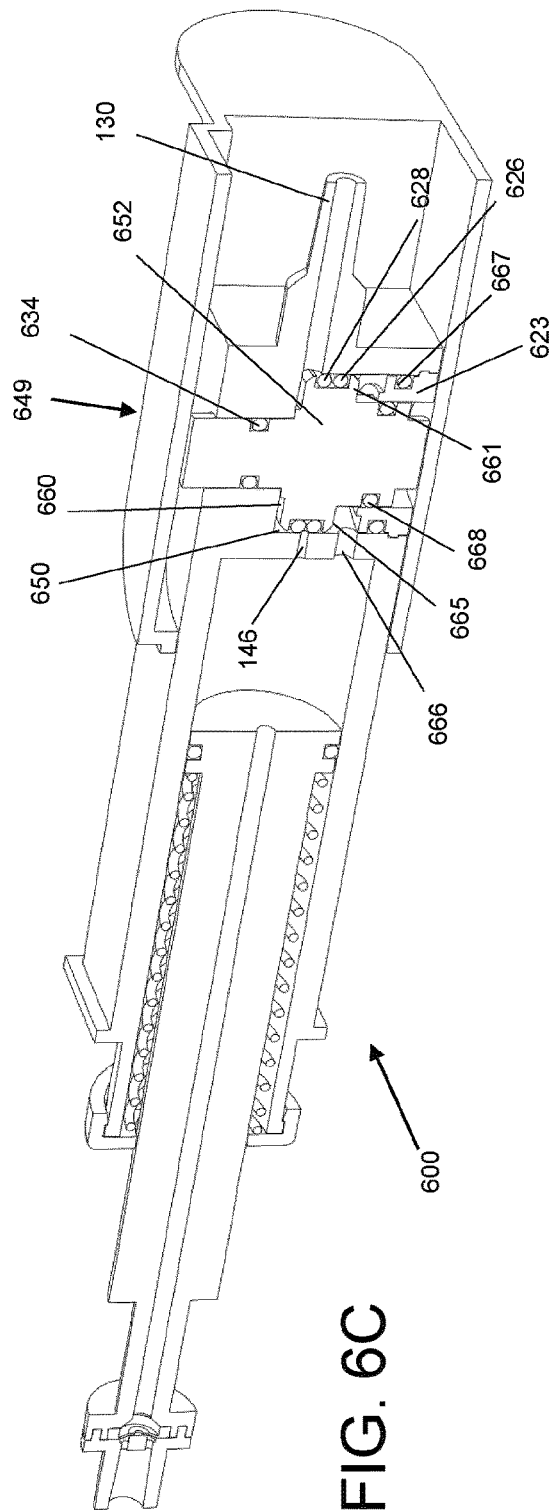

FIGS. 6A-6C illustrate another epidural device 600 that can utilize a differential pressure trigger mechanism 649, but is otherwise similar to device 100. In this example embodiment, the trigger spring has been replaced by a trigger reservoir 665, which is connected to the syringe reservoir chamber 144 by a relatively wide reservoir connector 666. The trigger piston 652 is moveable vertically and may be constrained by the trigger cap 623 at the bottom. Similar to device 100, the trigger chamber 650 may be bound by the priming seal 634 and the upper disk seal 628. The trigger reservoir 665 may be bound by the lower disk seal 626 and the trigger reservoir seal 668, as well as the trigger cap 623 and its associated trigger cap seal 667.

The operation of the differential pressure device 600 relies upon the differential forces on the trigger piston 652 from the trigger chamber 650 and trigger reservoir 665. The size of the horizontal faces on the trigger piston 652 can be relatively large for the trigger chamber face 660, and can be relatively smaller for the trigger reservoir face 661, which can create differential forces when the chambers 650 and 144 are at the same or nearly equivalent pressures. Details of the operation of this device are explained below.

Additional Designs

Figure 7A:
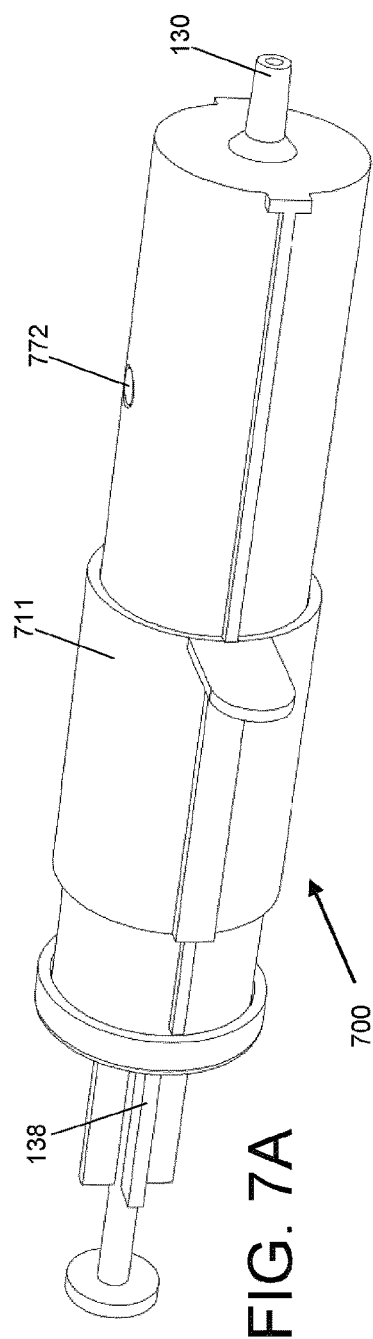
FIGS. 7A-7C illustrate an embodiment of the device which uses two trigger pins, one on the top and another on the bottom of the device, to engage the sliding pusher with the device.
Figure 7B:
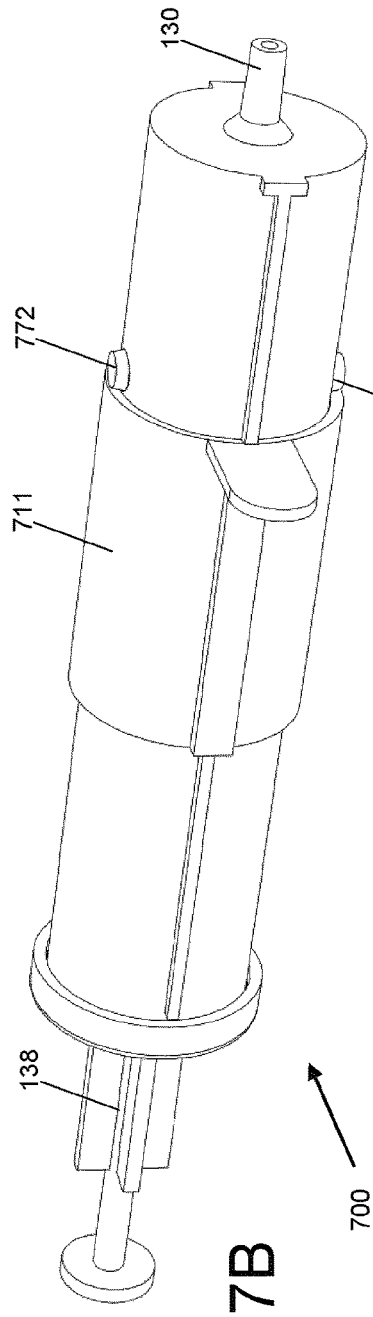
Figure 7C:
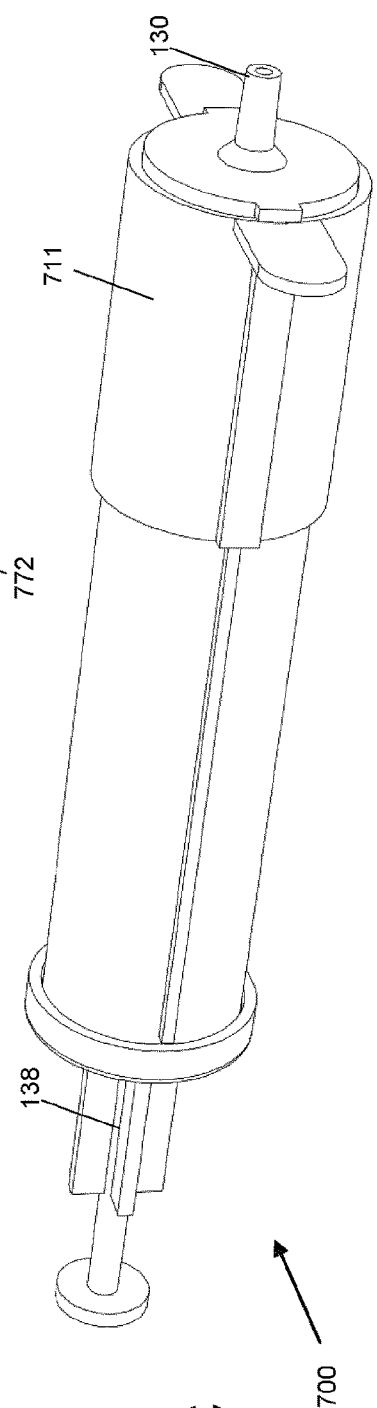

FIGS. 7A-7C show another epidural device 700 that is functionally similar to the device 100 shown in FIG. 1 but uses two piston pins 772 that when pressurized can move outwardly from both the top and bottom of the device 700 and inhibit or substantially prevent forward movement of the pusher 711 once the pusher 711 abuts the pins 772. The contact angle between the pins and the pusher may be such that the piston pins can move up and down in response to pressure changes in the chamber. When the epidural space is reached, the device can depressurize, allowing the piston pins 772 to slide inward and the pusher 711 to slide forward.

FIG. 7A shows the device 700 in an unprimed state, with the piston pins 772 retracted. FIG. 7B shows the device 700 in a primed state, with the piston pins 772 extended and stopping the forward travel of the pusher 711. FIG. 7C shows the device 700 in a triggered state and with the pusher slid fully forward. When the primed device is unblocked, (e.g., resulting from entry of the epidural needle 147 (not shown) into the epidural space), pressure in the internal chamber may be reduced and the piston pins 772 can move inwardly, allowing the pusher 711 to move forward.

Figure 8A:
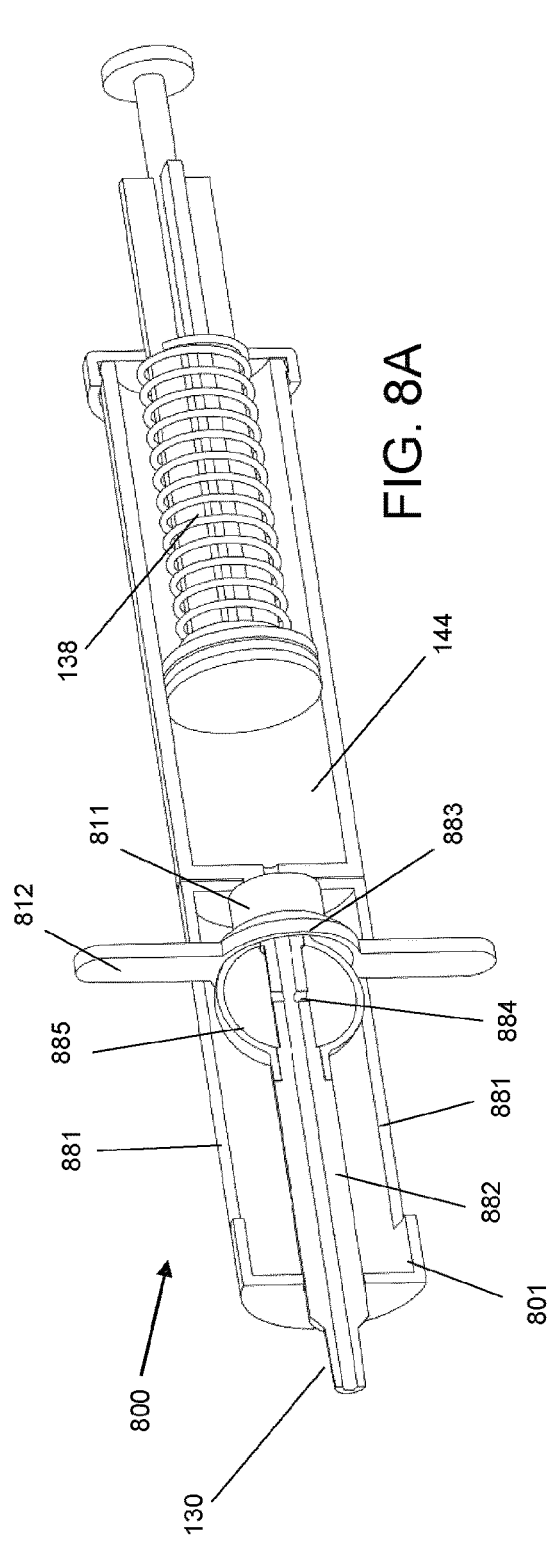
FIGS. 8A and 8B illustrate an embodiment of the device which uses a flexible membrane mechanism and trigger ring to engage the sliding pusher with the body of the device.
Figure 8B:
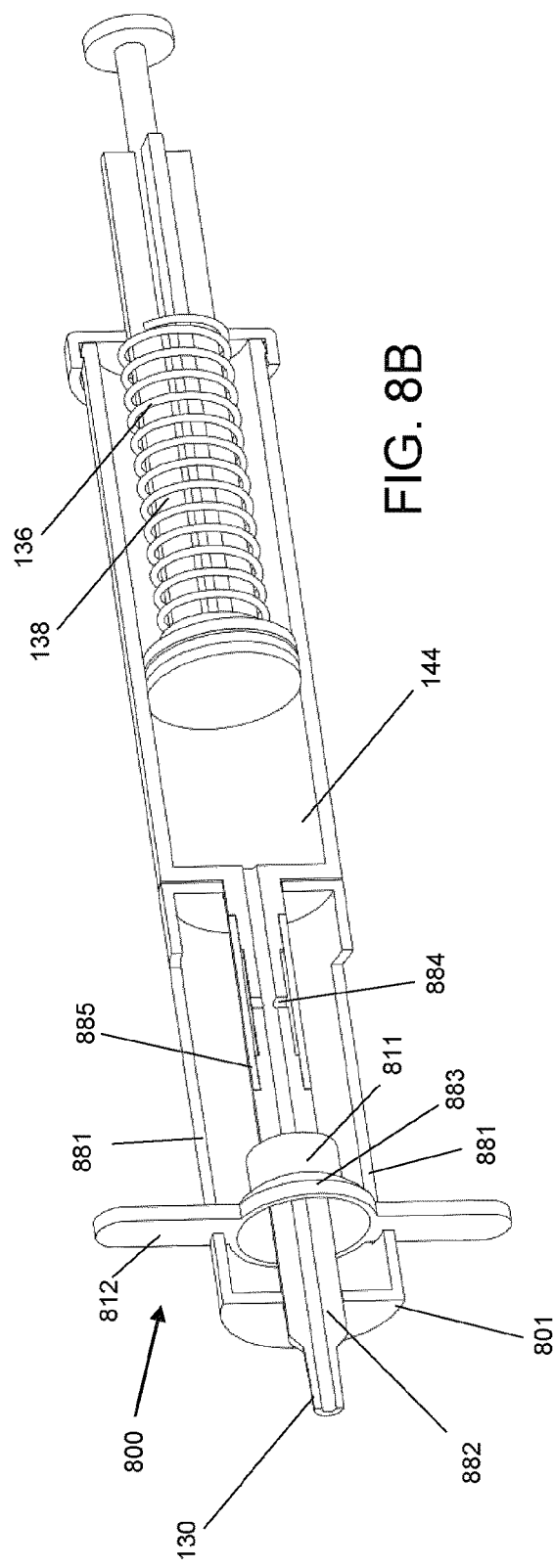

FIGS. 8A and 8B depict another epidural device 800 that is functionally similar to device 100. The epidural device 800 comprises a syringe body 801 having slits 881 defined therein. The body 801 has a tube 882 provided coaxially therein. The slits 881 may permit longitudinal movement of a pusher 811 that is at least partially contained within the body 801. The pusher 811 comprises a ring 883 provided on an outer circumference of the tube 882. The ring 883 is slidable in the axial direction along the tube 882 and may have two wings 812 connected thereto that extend out of the body 801 through the slits 881. The pusher 811 is slidable coaxially to and within the body 801 by applying force to the wings 812. The tube 882 can have at least one hole 884 defined therein for permitting fluid communication between can exit the tube 882 and enter a membrane 885 surrounding the hole. The membrane can expand and deflate in response to pressurization, and is shown in its inflated (pressurized) state in FIG. 8A.

When the epidural needle 147 (not shown) enters the epidural space, loss of pressure may cause the membrane 885 to deflate, thereby enabling movement of the ring 883 and thus the pusher 811. As the pusher 811 slides over the deflated membrane as shown in FIG. 8B, a majority of the force exerted on the pusher 811 will not be transferred to the needle 147 and thus further advancement of the needle 147 can be inhibited.

FIGS. 9A-9D depict yet another example embodiment of an epidural device 900. Similar to the device 800, the device 900 comprises a syringe body 901 having slits 981 defined therein. The body 901 has a tube 982 provided coaxially therein. The slits 981 may permit longitudinal movement of a pusher 911 contained at least partially within the body 901. The pusher 911 comprises a sleeve 992 slidably disposed on an outer circumference of the tube 982. The sleeve 992 is slidable in the axial direction along the tube 982 and may have two wings 912 connected thereto that extend out of the body 901 through the slits 981. The pusher 911 is slidable coaxially to and within the body 901 by applying force to the wings 912. The tube 982 may have at least one hole 984 through which fluid can exit the tube 982 toward a flexible or compliant section 991 of the tube 982 surrounding the hole. The flexible section 991 can be made from plastic or another flexible material and may bend and bow outwardly when exposed to an increase in fluid pressure. As discussed with respect to the previous example embodiments, pressure within the tube 982 can increase when the device 900 is filled with fluid and there is no flow or substantial resistance to flow out the needle 147 (not shown). When pressurized, the flexible section 991 can expand to press against a pusher sleeve 992 surrounding the section 991, thereby forming a frictional bond between the pusher sleeve 992 and the flexible section 991 which can allow advancement of the needle in response to force application on the wings 912 extending radially out from the pusher 911. This state is shown in FIG. 9A, and can be seen in detail in FIG. 9C.

When the epidural space is reached, pressure within the device 900 is reduced, causing the flexible portion 991 to collapse and thereby disengage the sleeve 992. The device 900 in this triggered state is shown in FIG. 9B, and can be seen in detail in FIG. 9D. The sleeve 992, and thus the pusher 911, now disengaged, can move freely of the needle 147 and thus further advancement of same is stopped.

Rather than being removably attachable, the needle 147 can be physically integrated with any of the devices of the present disclosure.

Operation of Loss of Pressure Designs (FIGS. 1-5)

The operation of the epidural device 100 will be described below. As indicated above, the devices 100, 300, 400 and 500 have a number of similar features; thus, their operation is similar. The discussion of the devices 300, 400 and 500 is limited to features not included in the device 100.

When the trigger piston 133 is at the upper end of the trigger barrel 131, the trigger pin 122 is retracted within the exterior surface of the trigger cap 123 and thus may not impede the sliding motion of the pusher 111. This is the unprimed or triggered position and is the default state for the device. In this position the restrictor 146 is substantially aligned with the space between the two disk seals 126 and 128 of the trigger piston 133, and fluid flow between the reservoir chamber 144 and the trigger chamber 150 may be substantially or completely prevented.

When the trigger piston 133 is at the bottom end of the trigger barrel 131 the trigger pin 122 extends beyond the exterior surface of the trigger cap 123 and may impede the forward sliding motion of the pusher 111. This is referred to herein as the primed position. To move the trigger piston 133 to this position in the devices 100 and 500, one may compress the trigger spring 124 by pressing on the priming button 114. The piston can be moved to such position in the devices 300 and 400 by moving the pusher forward and sliding the pusher back, respectively. In this position the restrictor 146 is aligned with the trigger chamber 150, allowing fluid communication between the reservoir and trigger chambers 144 and 150, respectively.

When the device is mostly or completely filled with fluid and the epidural needle 147 attached to the exit port 132 at the needle connector end 130 is blocked or sufficiently resistant to outflow of fluid (e.g. when the needle 147 is in a dense ligament), there may be little or no flow through the restrictor 146 and therefore no pressure drop from the reservoir chamber 144 to the trigger chamber 150. In this state, the forces due to the chamber pressure in the trigger chamber 150 may keep the trigger mechanism 149 in the primed position. When the epidural needle 147 is "unblocked" (i.e., when resistance to fluid outflow decreases sufficiently), flow through the restrictor may occur and result in a corresponding pressure drop across the restrictor 146, reducing the pressure in the trigger chamber 150 relative to the reservoir chamber 144. When the pressure in the trigger chamber 150 drops below the pressure required to keep the trigger spring 124 compressed and the trigger piston 133 in the primed position, the trigger spring 124 can push the trigger piston 133 into the triggered position. In such position, the trigger pin 122 may disengage the sliding pusher 111. This, in turn, may automatically inhibit or prevent further advancement of the epidural needle 147 into the epidural space.

Preferably, the restrictor 146 is sized such that a slow outflow of fluid from the needle 147 can occur without triggering the device. This may prevent the device 100 from triggering before the needle 147 enters the epidural space.

Operation of Differential Pressure Epidural Device (FIG. 6)

Once the device 600 is filled with fluid and primed, and when the epidural needle 147 is at least partially blocked as described above, such as by the needle tip being in ligament, there is no or little flow and thus no (or a negligible) pressure drop across the restrictor 146 so the trigger reservoir 665 and trigger chamber 650 pressures are approximately equal. When the chamber (665 and 650) pressures are equal there may be a greater force on the trigger chamber 650 side of the trigger piston 652 due to the larger area of the trigger chamber face 660, and thus the device 600 may remain in the primed position. In this position, the trigger pin 622 may impede axial movement the pusher. When the epidural needle is "unblocked" (i.e., when resistance to fluid outflow decreases sufficiently) while the device is filled or nearly filled with fluid there may be fluid flow and a pressure drop across the restrictor 146 so the trigger reservoir 665 pressure may be greater than the trigger chamber 650 pressure. If the difference in pressure is great enough the force on the smaller face 661 (trigger reservoir) of the trigger piston will overcome the force on the larger face 660 (trigger chamber) and the trigger piston 652 can move to the triggered position where the trigger pin 622 may not impede the pusher from sliding axially toward the needle connector end 130.

However, if there is a sufficiently slow flow of fluid from the epidural needle 147 (e.g. into muscle tissue), the pressure drop across the restrictor may be negligible, and the resulting forces on the trigger piston 652 may not cause premature triggering. If the epidural needle 147 becomes "blocked" again and there is still pressurized fluid in the reservoir 144, the trigger piston 652 may be returned to the primed position by pressing the priming button 614. If the device runs out of fluid, the forces on each the faces of the trigger piston can both decrease to zero, and the trigger piston 652 may stay in its last, or most recent position because there will be no fluid pressure driving it in either direction. In this case, the device 600 may fail to trigger even if the needle 147 reaches the epidural space. This may be overcome by incorporating a slanted pin (not shown) within the reservoir plunger 138 that can interact with the piston 652 to force the piston 652 upwardly when the reservoir 144 runs out of fluid, thereby disengaging the trigger pin 622 from the pusher 111.

Each of the devices 700, 800, and 900, are operated in a similar fashion as described above, using variations on the trigger mechanism and pusher configuration. While not shown, the trigger mechanisms in devices 700, 800 and 900 could be combined with features similar to those described with reference to FIGS. 1A-1D and 3A-5 to achieve similar triggering responses, e.g., limiting fluid flow out of the exit port into the patient to reduce the likelihood of premature triggering.

The automatic disengaging mechanism of the epidural device described herein may have other applications not discussed above. Without being held to any theory, it is believed that a needle and syringe device including a disengaging mechanism according to the present disclosure could be configured for other medical applications. More generally, the automatic disengaging mechanism described herein may be applied when it is desirable to pass a needle through one or more materials having a relatively high resistance to outflow from the needle into a material having a relatively lower resistance to outflow, and to ultimately inhibit or prevent unwanted advancement of the needle beyond the low resistance material. The present description is not limited to any particular triggering mechanism for causing the pushing means to disengage from the epidural needle.

For simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

Although the above principles have been described with reference to certain specific examples, various modifications thereof will be apparent to those skilled in the art as outlined in the appended claims.

The invention claimed is:

1. An epidural device comprising:
   an elongate body with a longitudinal axis;
   an inlet;
   an outlet being removably attachable to a needle having a passage therethrough;
   a sleeve slidably disposed about an outer surface of the body;
   a first chamber defined in the body, the first chamber being configured to receive a fluid;
   a second chamber defined in the body, the second chamber being configured to convey the fluid to the outlet;
   a flow restrictor between the first and second chambers for providing fluid communication therebetween, wherein the flow restrictor has a smaller diameter than a diameter of the outlet;
   the first chamber having a first biasing mechanism positioned therein for pressurizing the first chamber;
   the second chamber having a piston provided therein, the piston being movable between:
      a primed position, where the piston is moved away from the flow restrictor, and the fluid can pass between first and second chambers; and
      a triggered position, where the piston covers the flow restrictor, and the fluid can exit the second chamber via the outlet;
   wherein:
      in the primed position, the sleeve is engageable by an extension of the piston to inhibit the sleeve from moving axially toward the outlet; and
      in the triggered position, the sleeve is not engageable by the extension of the piston and the sleeve is movable axially toward the outlet.

2. The device of claim 1, wherein the first chamber is configured to receive the fluid from the inlet, has an opening therein opposite the flow restrictor, and the device further comprises a plunger extending into the chamber through the opening, the plunger having:
   a flow port defined therein for providing fluid communication between the inlet and the first chamber;
   a distal end positioned within the first chamber; and
   a proximal end positioned outside of the chamber and being adapted to engage the inlet.

3. The device of claim 1, wherein the first chamber has an opening therein opposite the flow restrictor, and the device further comprises a plunger extending into the chamber through the opening, the plunger having:
   a distal end positioned within the first chamber; and
   a proximal end positioned outside of the chamber.

4. The device of claim 2, wherein the first biasing mechanism is a spring provided within the chamber and around the plunger intermediate the distal end thereof and the opening of the chamber.

5. The device of claim 3, wherein a filling port for filling the first chamber extends between the first and second chambers, the filling port including a one-way valve to permit flow from the second chamber to the first chamber.

6. The device of claim 1, wherein the flow restrictor is sized such that, when the device is in the primed position, at least some of the fluid can exit the second chamber through the outlet without triggering the device.

7. The device of claim 1, wherein a second biasing mechanism is located within the second chamber, the second biasing mechanism being weaker than the first biasing mechanism.

8. The device of claim 7, wherein the second biasing mechanism is a spring.

9. The device of claim 1, wherein the piston includes a disk extending radially therefrom, the disk dividing the first chamber into trigger and reservoir chambers and having first and second annular surfaces in the trigger chamber and the reservoir chamber, respectively, the reservoir chamber being capable of fluid communication with the first chamber via a flow channel extending therebetween, wherein:
   when the device is in the primed position, the disk is positioned intermediate the flow channel and the flow restrictor and the trigger chamber can fluidly communicate with the first chamber and the outlet; and
   when the device is in the triggered position, the disk covers the flow restrictor and the trigger chamber cannot fluidly communicate with the first chamber.

10. The device of claim 9, wherein the first annular surface has a greater surface area than a surface area of the second annular surface such that a force differential is created between the trigger and reservoir chambers.

11. The device of claim 1, wherein the piston includes, on an end thereof opposite the extension, a button pressable by a user in a direction toward the extension to prime the device.

12. The device of claim 1, wherein the sleeve includes a protrusion extending therefrom toward the body of the device, the protrusion being configured to prime the device by depressing a button of the piston when the sleeve slides thereover, the button being attached to an end of the piston opposite the extension.

13. An epidural device comprising:
   an elongate body with a longitudinal axis;
   an inlet;
   an outlet being removably attachable to a needle having a passage therethrough;
   a sleeve slidably disposed about an outer surface of the body;
   a fluid passage defined in the body, the fluid passage being configured to receive a fluid from the inlet;
   a pressure chamber defined in the body, the chamber being configured to convey the fluid to the outlet;
   a flow restrictor between the fluid passage and the pressure chamber for providing fluid communication therebetween, the flow restrictor having a smaller diameter than a diameter of the outlet;
   the pressure chamber having a piston provided therein, the piston being movable between:
      a primed position, where the piston is moved away from the flow restrictor, and the fluid can pass between the fluid passage and the pressure chamber; and a triggered position, where the piston covers the flow restrictor, and the fluid can exit the pressure chamber via the outlet;

wherein:

in the primed position, the sleeve is engageable by an extension of the piston to inhibit the sleeve from moving axially toward the outlet; and in the triggered position, the sleeve is not engageable by the extension of the piston and the sleeve is movable axially toward the outlet.

14. An epidural device comprising:

an elongate body with a longitudinal axis;

an inlet;

an outlet being removably attached to a needle having a passage therethrough;

a sleeve slidably disposed on an outer surface of the body;

the body having a chamber defined therein for communicating a fluid between the inlet and the outlet;

a biasing mechanism for pressurizing the chamber;

a trigger mechanism for engaging the sleeve, the trigger mechanism being contained at least partially within the chamber and being movable between a first position and a second position by a decrease in pressure in the chamber; wherein:

in the first position, the sleeve is engageable by the trigger mechanism to inhibit the sleeve from moving axially toward the outlet; and in the second position, the sleeve is not engageable by the trigger mechanism and the sleeve is movable axially toward the outlet.

15. The device of claim 14, wherein the trigger mechanism comprises at least one piston having first and second ends, the first end being positioned in the chamber such that the first end can be acted on by the biasing mechanism, the second end extending radially outward through the body, wherein:

in the first position, the second end protrudes radially from the body to an extent that the sleeve is engageable by the second end; and in the second position, the second end is positioned closer to the body than when the device is the first position, such that the sleeve is not engageable by the second end.

16. The device of claim 14, wherein the trigger mechanism comprises an inflatable membrane that can be inflated by the biasing mechanism, wherein:

in the first position, the inflatable membrane is inflated to an extent that the sleeve is engageable by the membrane; and in the second position, the inflatable membrane is deflated to an extent that the sleeve is not engageable by the membrane.

17. The device of claim 14, wherein the trigger mechanism comprises a compliant component that can be expanded by the biasing mechanism, wherein:

in the first position, the compliant component is expanded to an extent that the sleeve is engageable by the component; and in the second position, the compliant component is retracted to an extent that the sleeve is not engageable by the compliant component.

18. An epidural device comprising:

an elongate body with a longitudinal axis;

an inlet;

an outlet being removably attachable to a needle having a passage therethrough;

a chamber defined by the body, the chamber being for communicating a fluid between the inlet and the outlet;

a holdable surface mounted about the body, the holdable surface being selectively movable along the longitudinal axis;

a disengagement mechanism for selectively engaging the holdable surface, the disengagement mechanism being movable between a first position and a second position; wherein:

in the first position, the disengagement mechanism engages the holdable surface to inhibit the holdable surface from moving axially toward the outlet, thereby facilitating advancement of the needle by advancement of the holdable surface; and in the second position, the holdable surface is moveable axially toward the outlet, and advancement of the needle by advancement of the holdable surface is inhibited;

the holdable surface including a sleeve slidably disposed on an outer surface of the body and the disengagement mechanism comprising:

a trigger mechanism for engaging the sleeve, the trigger mechanism being contained at least partially within the chamber and being movable between the first position and the second position by a decrease in pressure in the chamber; wherein:

in the first position, the sleeve is engageable by the trigger mechanism to inhibit the sleeve from moving axially toward the outlet; and in the second position, the sleeve is not engageable by the trigger mechanism and the sleeve is movable axially toward the outlet;

and a biasing mechanism for pressurizing the chamber.

19. The device of claim 18, wherein the trigger mechanism comprises at least one piston having first and second ends, the first end being positioned in the chamber such that the first end can be acted on by the biasing mechanism, the second end extending radially outward through the body, wherein:

in the first position, the second end protrudes radially from the body to an extent that the sleeve is engageable by the second end; and in the second position, the second end is positioned closer to the body than when the device is the first position, such that the sleeve is not engageable by the second end.

* * * * *